(12) United States Patent
Park et al.

(10) Patent No.: US 11,390,648 B2
(45) Date of Patent: Jul. 19, 2022

(54) PEPTIDE

(71) Applicant: HYSENSBIO, Gwacheon-si (KR)

(72) Inventors: Joo Hwang Park, Incheon (KR); Ji Hyun Lee, Seoul (KR)

(73) Assignee: HYSENSBIO, Gwacheon-si (KR)

( * ) Notice: Subject to any disclaimer, the term of this patent is extended or adjusted under 35 U.S.C. 154(b) by 0 days.

(21) Appl. No.: 16/956,754

(22) PCT Filed: Dec. 17, 2018

(86) PCT No.: PCT/KR2018/016011
§ 371 (c)(1),
(2) Date: Jun. 22, 2020

(87) PCT Pub. No.: WO2019/132352
PCT Pub. Date: Jul. 4, 2019

(65) Prior Publication Data
US 2021/0061855 A1  Mar. 4, 2021

(30) Foreign Application Priority Data

Dec. 28, 2017 (KR) .......................... 10-2017-0182322
Jul. 6, 2018 (KR) .......................... 10-2018-0078548

(51) Int. Cl.
| | | |
|---|---|---|
| *C07K 7/06* | (2006.01) | |
| *A23L 33/18* | (2016.01) | |
| *A61P 1/02* | (2006.01) | |
| *A61K 38/00* | (2006.01) | |

(52) U.S. Cl.
CPC ............... *C07K 7/06* (2013.01); *A23L 33/18* (2016.08); *A61P 1/02* (2018.01); *A61K 38/00* (2013.01)

(58) Field of Classification Search
None
See application file for complete search history.

(56) References Cited

U.S. PATENT DOCUMENTS

| | | |
|---|---|---|
| 6,046,164 A | 4/2000 | Asano et al. |
| 2011/0020299 A1 | 1/2011 | Bader |
| 2018/0179254 A1 | 6/2018 | Park et al. |

FOREIGN PATENT DOCUMENTS

| | | |
|---|---|---|
| JP | 2012-513427 A | 6/2012 |
| JP | 2012-528891 A | 11/2012 |
| JP | 6715446 B2 | 7/2020 |
| JP | 2020-127420 A | 8/2020 |
| KR | 10-1995-703993 A | 11/1995 |
| KR | 10-2011-0019106 A | 2/2011 |
| KR | 10-1343460 B1 | 12/2013 |
| KR | 10-1370023 B1 | 3/2014 |
| KR | 10-1510941 B1 | 4/2015 |
| KR | 10-2016-0014184 A | 2/2016 |
| KR | 10-1627917 B1 | 6/2016 |
| KR | 10-1756740 B1 | 7/2017 |
| KR | 10-1772449 B1 | 8/2017 |
| KR | 101772449 * | 8/2017 |
| RU | 2 491 076 C2 | 8/2013 |
| RU | 2 719 434 C1 | 4/2020 |

OTHER PUBLICATIONS

International Search Report of PCT/KR2018/016011 dated Mar. 18, 2019 [PCT/ISA/210].
Kanie et al., "Amino acid sequence preferences to control cell-specific organization of endothelial cells, smooth muscle cells, and fibroblasts", Journal of Peptide Science, Feb. 24, 2011, vol. 17, pp. 479-486 (total 8 pages).
Kanie et al., "Amino acid sequence preferences to control cell-specific organization of endothelial cells, smooth muscle cells, and fibroblasts", J. Pept. Sci., vol. 17, pp. 479-486, 2011 (9 pages total).

* cited by examiner

*Primary Examiner* — Sergio Coffa
(74) *Attorney, Agent, or Firm* — Sughrue Mion, PLLC

(57) ABSTRACT

A novel peptide and a composition including the peptide are disclosed. The composition may be a pharmaceutical composition, a quasi-drug composition, a dietary supplement, or a food composition. A polynucleotide encoding the peptide and an expression vector including the polynucleotide are also disclosed. The peptide promotes regeneration of hard tissue and is useful for treating dentin-dental pulp diseases or periodontal diseases.

10 Claims, 16 Drawing Sheets

Specification includes a Sequence Listing.

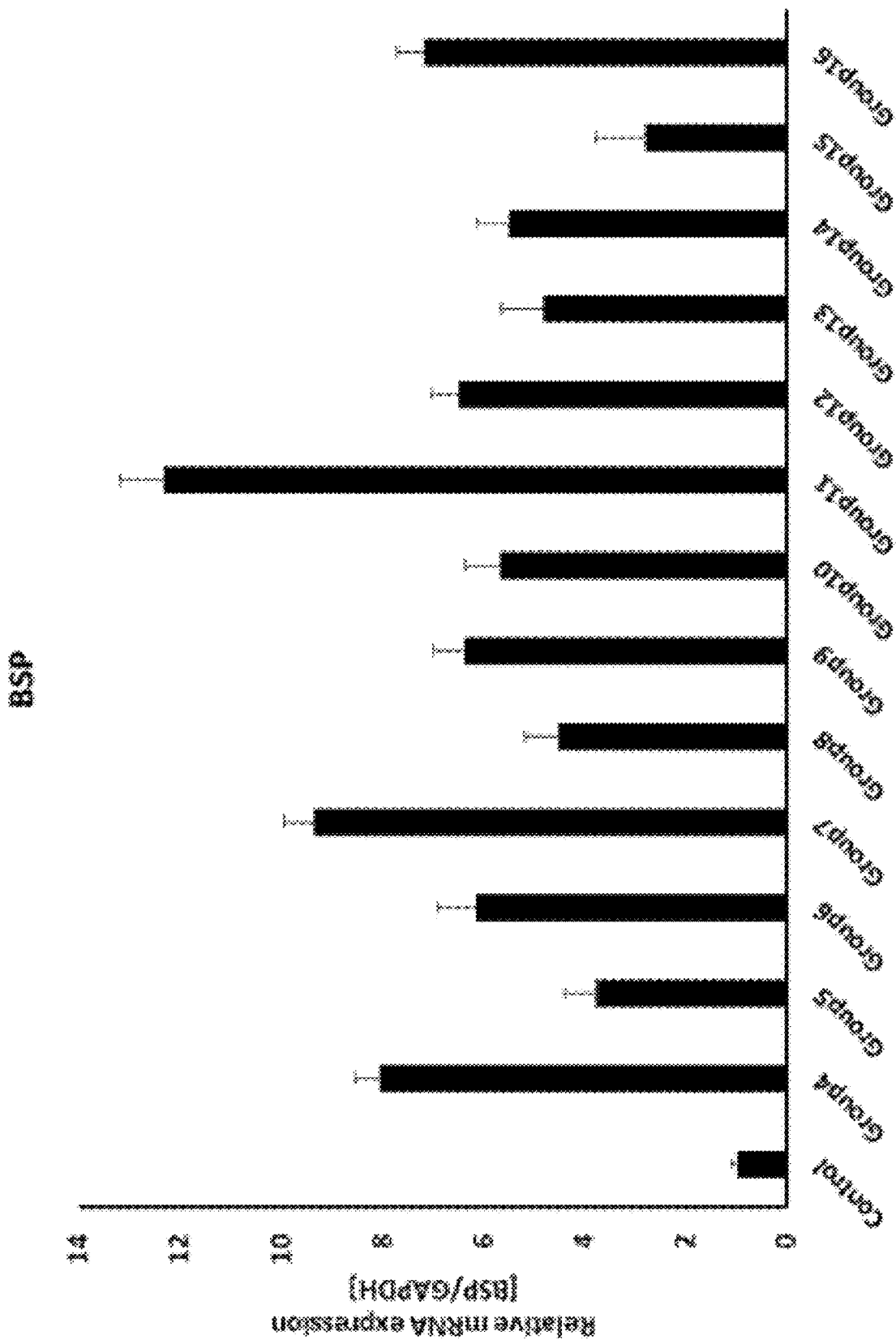

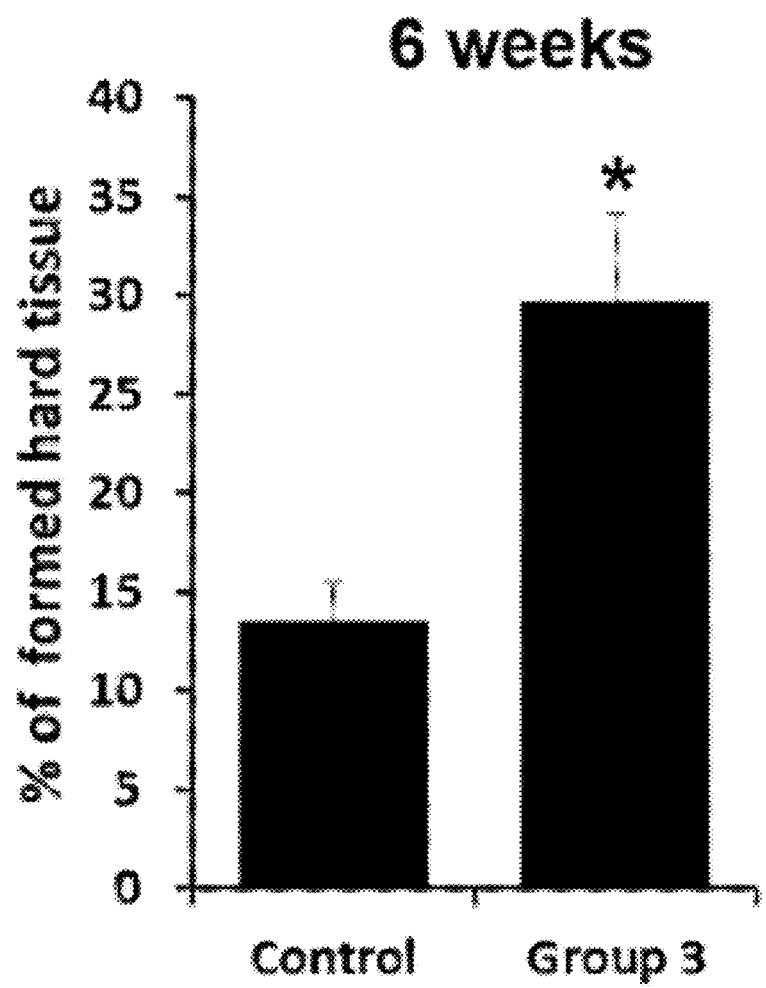

PEPTIDE

CROSS REFERENCE TO RELATED APPLICATIONS

This application is a National Stage of International Application No. PCT/KR2018/016011, filed Dec. 17, 2018, claiming priorities to Korean Patent Application No. 10-2017-0182322, filed Dec. 28, 2017 and Korean Patent Application No. 10-2018-0078548, filed Jul. 6, 2018.

BACKGROUND OF THE INVENTION

1. Field of the Invention

The present invention relates to a novel peptide, and more particularly, to a peptide for promoting regeneration of hard tissue and/or dental pulp tissues and treating dentin-dental pulp diseases, and/or periodontal diseases, a polynucleotide encoding the peptide, an expression vector comprising the polynucleotide, and a pharmaceutical composition for preventing or treating dentin-dental pulp diseases and/or periodontal diseases comprising the peptide, a quasi-drug composition for preventing or alleviating dentin-dental pulp diseases and/or periodontal diseases comprising the peptide, and a health functional food composition for preventing or alleviating dentin-dental pulp diseases and/or periodontal diseases including the peptide.

2. Description of the Related Art

Dental pulp is a richly innervated and vascularized soft connective tissue that occupies the pulp chamber inside a tooth and extends to the outer surface of the dentin. Disorders occurring in the dental pulp are called dental pulp diseases.

There are many causes of dental pulp diseases, but in most cases, dental pulp diseases are caused by a bacterial infection due to dental caries, or infections in the dental pulp through the perforation, fracture, cracks, or periodontal pocket. External wounds, abrasion, tooth cracks, or friction or heat from dental equipment may also cause dental pulp diseases. The pulpitis caused by bacterial infection may lead to root apex and periodontal diseases. Dental pulp diseases successively progress to pulp hyperemia, pulpitis, and pulp necrosis. Pulp necrosis may lead to periapical diseases or disorders to the entire tooth because the death of the dental pulp prevents the blood supply to the dental pulp and thus the entire pulp tissue is lost.

For treatment of the pulp or periapical diseases, pulp capping materials and pulp canal filling materials are used, and calcium hydroxides, MTA (Mineral Trioxide Aggregate), Gutta-percha, etc., has been generally used. MTA shows therapeutic effects because it has a leakage sealing ability and biocompatibility. However, the use of MTA is hampered due to its relatively high cost as a dental repair material and discoloration, leading to an esthetic problem. Gutta-percha is relatively low cost and has excellent flow characteristics. However, it is not a physiologically acceptable method which causes a loss of viability of the pulp. Up to now, conservative treatments for dentin and pulp diseases have problems of the weak or brittle teeth or reinfection.

Periodontal tissue (periodontium) is a complex organ composed of epithelial tissue, soft connective tissue, and calcified connective tissue. The structure of the periodontium is composed of the gingiva, periodontal ligament (PDL), cementum, and alveolar bone. Gingival fibroblast and periodontal ligament fibroblast are major cellular components of gingival soft connective tissue, and forming and maintaining an extracellular matrix. Additionally, the gingival fibroblast is mainly involved in maintaining the gingival connective tissue, while the periodontal ligament fibroblast has a unique function to form the periodontal ligament and is involved in the restoration and regeneration of adjacent alveolar bone and cementum in vivo. When periodontal disease occurs, clinically, the gingival bleeding and swelling, periodontal pocket formation, and destruction of the alveolar bone may result in dental loss.

Since the ultimate goal of treating periodontal disease is to restore damaged connective tissue, cementum and alveolar bone, for this purpose, not only regeneration of the periodontal ligament supporting the alveolar bone but also the regeneration of the alveolar bone and the cementum that can be attached by the periodontal ligament is needed.

Therefore, many studies have been actively conducted to develop therapeutic agents capable of effectively treating dentin-dental pulp diseases or periodontal diseases. For example, Korean Patent Publication No. 2012-0089547 discloses a composition for forming hard tissue or regenerating dentin or pulp tissues, including ameloblasts, apical bud cells, or cultures thereof as an active ingredient, and Korean Patent Publication No. 2009-0033643 discloses novel tooth stem cells derived from tooth follicles and a method of culturing the same. Furthermore, Korean Patent Publication No. 2016-0105627 discloses a pharmaceutical composition for treating periodontal disease comprising pre-ameloblast conditioned medium.

The present inventors had made many efforts to develop an agent capable of more effectively treating dentin-dental pulp diseases and/or periodontal diseases, causing damage to alveolar bone and cementum. As a result, they developed a peptide showing effects of treating a cell for promoting regeneration of hard tissue, including dentin, bone and cementum and/or dental pulp tissue, and treating dentin-dental pulp diseases and/or periodontal diseases, thereby completed the present invention.

SUMMARY OF THE INVENTION

Embodiments of the present inventive concepts may provide a peptide for promoting regeneration of hard tissue and/or dental pulp tissues and treating dentin-dental pulp diseases and/or periodontal diseases.

Embodiments of the present inventive concepts may also provide a polynucleotide encoding the peptide.

Embodiments of the present inventive concepts may also provide an expression vector, including the polynucleotide.

Embodiments of the present inventive concepts may also provide a pharmaceutical composition for preventing or treating dentin-dental pulp diseases and/or periodontal diseases, including the peptide.

Embodiments of the present inventive concepts may also provide a quasi-drug composition for preventing or alleviating dentin-dental pulp diseases and/or periodontal diseases, including the peptide.

Embodiments of the present inventive concepts may also provide a health functional food composition for preventing or alleviating dentin-dental pulp diseases and/or periodontal diseases, including the peptide.

Embodiments of the present inventive concepts may also provide a method of preventing or treating dentin-dental pulp diseases and/or periodontal diseases, the method including administering the composition including the peptide to a subject, excluding humans.

Embodiments of the present inventive concepts may also provide a method of promoting regeneration of hard tissue including dentin, bone, and cementum and/or dental pulp tissue, the method including administering the composition including the peptide to a subject. Embodiments of the present inventive concepts may also provide the use of a peptide for promoting regeneration of hard tissue and/or pulp tissue.

Embodiments of the present inventive concepts may also provide the use of a peptide in preventing or treating dentin-dental pulp diseases and/or periodontal diseases.

Embodiments of the present inventive concepts may also provide a peptide comprising an amino acid sequence of the following Formula 1:

K-Y-R1-R2-R3-R4-R5    (Formula 1)

wherein R1 and R2 are arginine(R), lysine(K), glutamine (Q) or asparagine(N), respectively;

R3, R4, and R5 are arginine(R) or lysine(K), respectively.

Embodiments of the present inventive concepts may also provide a peptide wherein R1 is glutamine(Q), R2 is arginine(R).

Embodiments of the present inventive concepts may also provide a peptide wherein R1 is arginine(R) or lysine(K), R2 is glutamine(Q).

Embodiments of the present inventive concepts may also provide a peptide wherein R1 and R2 are glutamine (Q), respectively.

Embodiments of the present inventive concepts may also provide a peptide wherein R1 is arginine (R) or lysine (K), and R2 is arginine (R).

Embodiments of the present inventive concepts may also provide a peptide wherein R1 is glutamine (Q), arginine (R) or lysine (K), and R2 is lysine (K).

Embodiments of the present inventive concepts may also provide a peptide wherein R1 is arginine (R), lysine (K), glutamine (Q) or asparagine(N), R2 is arginine (R), lysine (K), glutamine (Q) or asparagine (N), at least one of R1 or R2 is asparagine(N).

Embodiments of the present inventive concepts may also provide a peptide wherein the peptide is subjected to N- or C-terminal acetylation, amidation, or methylation; D-amino acid introduction; peptide bond modification including $CH_2-NH$, $CH_2-S$, $CH_2-S=0$, $CH_2-CH_2$; backbone modification; or side-chain modification.

Effect of the Invention

A peptide of the present invention exhibits excellent effects of promoting regeneration of hard tissue and/or pulp tissues. Therefore, it may be widely applied to the development of a variety of agents for preventing or treating dentin-dental pulp diseases or for preventing or treating periodontal diseases causing damage to bone and/or cementum.

BRIEF DESCRIPTION OF THE DRAWINGS

FIG. 2B is another graph showing the results of comparing the expression levels of the BSP, a bone and cementum differentiation marker gene, in human bone marrow-derived mesenchymal stem cells (hBMSCs) treated with the novel peptide of the present invention.

FIG. 3 shows the results of measuring the amount of newly formed hard tissue using human dental pulp cells (hDPCs) for 6 weeks in vivo.

DETAILED DESCRIPTION OF THE PREFERRED EMBODIMENTS

Figure 1A:
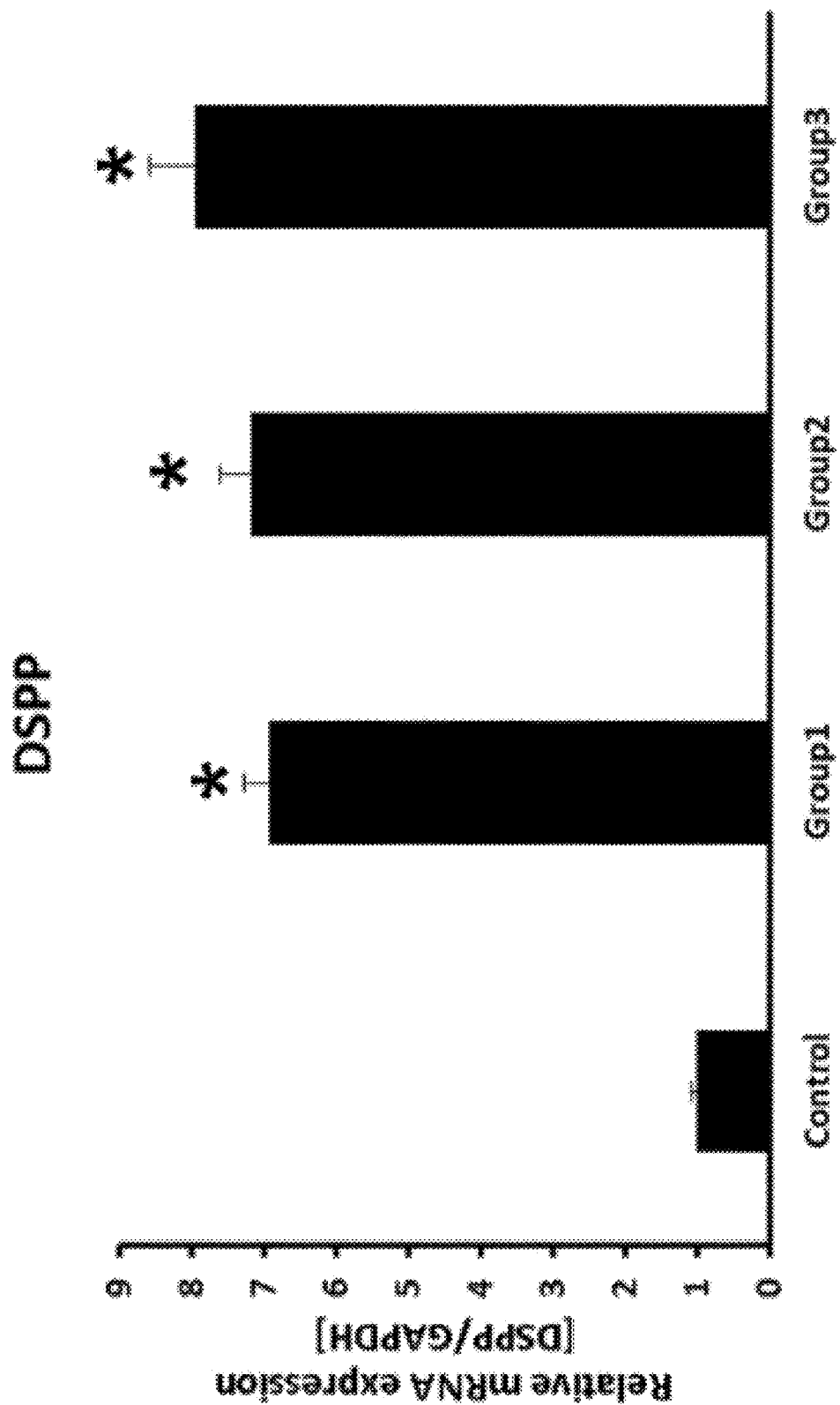
FIG. 1A is a graph showing the results of comparing the expression levels of the dentin sialophosphoprotein (Dspp), odontoblast differentiation marker gene, in human dental pulp cells (hDPCs) treated with the novel peptide of the present invention.

The present inventors conducted many studies to develop an agent capable of more effectively treating dentin-dental pulp diseases and/or periodontal diseases. As a result, they developed a novel peptide comprising or consisting of 7 amino acids.

The newly developed peptide was prepared by substitution of a part of an amino acid sequence of a peptide, which may exhibit a therapeutic effect on dentin or dental pulp diseases. It was confirmed that the newly developed peptide might increase expression levels of Dspp (Dentin sialophosphoprotein) and Nestin which are odontoblast differentiation marker genes, thereby showing an effect of promoting dentin regeneration, and it is moreover possible to increase the expression level of the BSP (Bone sialoprotein), which is a differentiation marker gene of osteoblasts and cementoblasts, thereby exhibiting an effect of promoting regeneration of bone and cementum.

Further, an implant including the peptide together with human dental pulp cells was prepared, and the prepared implant was transplanted into a subcutaneous tissue of an immunocompromised mouse, and after 6 weeks to 12 weeks, the transplanted tissue was analyzed. As a result, it was found that a dentin/pulp-like tissue having the most similar morphology to a dentin/dental pulp tissue in vivo was formed, bone-like tissue having the most similar morphology to a bone tissue in vivo was formed. A production level of collagen was increased, and the expression level of DSP, which is an odontoblast-specific differentiation marker, was increased.

Furthermore, the morphology of the transplanted tissue was examined under a scanning electron microscope. As a result, odontoblast-like cells along the formed hard tissue were observed, was confirmed that the dendritic cell processes also extend toward the formed hard tissue. Moreover, a typical characteristic was confirmed that osteoblast and/or cementoblast with a cubic cell-attached on the surface of the formed hard tissue.

Therefore, it can be seen that the peptide of the present invention may exhibit effects of promoting regeneration of hard tissue and/or dental pulp and treating dentin-dental pulp diseases and/or periodontal diseases. The peptide of the present invention having these effects has never been reported so far, and the present inventors first developed it.

In an aspect, the present invention provides a peptide for promoting regeneration of hard tissue and/or dental pulp and treating dentin-dental pulp diseases and/or periodontal diseases, the peptide including an amino acid sequence of the following Formula 1:

K-Y-R1-R2-R3-R4-R5 (Formula 1)

wherein R1, and R2 are arginine(R), lysine(K), glutamine (Q) or asparagine(N);

R3, R4, and R5 are arginine(R) or lysine(K), respectively.

The term "hard tissue", as used herein, refers to a relatively hard skeletal tissue including bone, hyaline cartilage, and fibrous cartilage. In one aspect, according to the present invention, the hard tissue may include dentin, bone, and cementum.

The term "dentin", as used herein, is also called dentine, and refers to a yellowish-white hard tissue that makes up most of a tooth. Dentin is not exposed to the surface of the tooth, because it is covered by enamel in the tooth crown and cementum in the root. However, dentin exposure may occur at the apical end, or the occlusal surface of the tooth crown as the enamel wears with aging. The dentin is a kind of bone-like tissue, but it is distinguished from a general bone tissue in that the cell bodies of the dentin stay in the dental pulp while their processes extend into the dentinal tubules.

The term "cementum" of the present invention refers to a thin film of a form in which the bones covering the tooth roots (root roots) and other parts of a mammal are slightly deformed. The cementum is composed of 50% inorganic and 50% moisture-organic, yellow in color, and exhibits lower hardness than dentin or enamel. The cementum includes periodontal ligament fibers that fix the teeth to the alveolar bone, and when bacteria are infected with the gums, the degeneration of the cementum surrounding the teeth occurs, and the deformed cementum periodontal ligament fibers that connect the teeth and the alveolar bones do not stick to the teeth and the teeth will be shaken. In order to treat such degeneration of cementum, a method is used to remove the degenerated cementum and promote the formation of new cementum.

The peptide of the present invention is characterized in that it may increase expression levels of Dspp, and Nestin genes which are odontoblast differentiation marker genes, the expression level of the BSP (Bone sialoprotein) genes which are differentiation marker genes of osteoblasts and cementoblasts, and when the peptide is transplanted together with human dental pulp cells, the human dental pulp cells form a dentin/dental pulp-like tissue and bone-like tissue.

The peptide of the present invention includes peptide variants thereof having a sequence including one or more amino acid residues different from those of the amino acid sequence of the peptide of the present invention, as long as it may promote regeneration of hard tissue like dentin, bone and cementum and/or dental pulp and exhibit a therapeutic effect on dentin-dental pulp diseases and/or periodontal diseases.

Amino acid exchanges in proteins and polypeptides, which do not generally alter the molecular activity, are known in the art. The most commonly occurring exchanges are amino acid residues Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, Asp/Gly, in both directions. The peptide may include peptides that have improved structural stability against heat, pH, etc., or improved ability to promote regeneration of hard tissue like dentin, bone, and cementum and/or dental pulp due to alteration or modification of the amino acid sequence.

Amino acid variations are made based on the relative similarity of amino acid side-chain substituents, such as hydrophobicity, hydrophilicity, charge, size, and the like. Since all seven amino acids comprising the peptide of the present invention correspond to hydrophilic amino acids, the relative similarity of amino acid side chain substituents is high. Accordingly, even if the amino acids comprising the peptide of SEQ ID NO: 1 are substituted with various amino acids having hydrophilic properties, the effect of the peptide provided by the present invention can be exhibited as it is due to its structural similarity. For example, although glutamine which is an acidic amino acid at position 3 of the peptide of SEQ ID NO: 1 of the present invention is substituted with an acidic amino acid, asparagine, or a basic amino acid, lysine or arginine, the effects of the peptide of the present invention may be obtained as it is; although arginine which is a basic amino acid at position 4 of the peptide of SEQ ID NO: 1 is substituted with a basic amino acid, lysine or an acidic amino acid, glutamine or asparagine, the effects of the peptide of the present invention may be obtained as it is; although arginine which is a basic amino acid at position 5 of the peptide of SEQ ID NO: 1 is substituted with a basic amino acid lysine, the effects of the peptide of the present invention may be obtained as it is; although lysine which is a basic amino acid at position 6, or 7 of the peptide of SEQ ID NO: 1 is substituted with a basic amino acid arginine, the effects of the peptide of the present invention may be obtained as it is.

As such, although the acidic amino acids or basic amino acids comprising the peptide of the present invention are substituted with amino acids having the same properties, or substituted with different acidic amino acids or basic amino acids, respectively, the effects of the peptide of the present invention may be obtained as it is. Therefore, it is apparent that a peptide variant having a sequence including one or more amino acid residues different from those of the amino acid sequence constituting the peptide of the present invention is also included in the scope of the peptide of the present invention.

Further, although arbitrary amino acids are added at the N-terminus or C-terminus of the peptide of the prevention, the effects of the peptide of the present invention may be obtained as it is. Therefore, a peptide prepared by adding arbitrary amino acids at the N-terminus or C-terminus of the peptide of the present invention is also included in the scope of the peptide of the present invention. For example, a peptide prepared by adding 1 to 300 amino acids at the N-terminus or C-terminus of the peptide of the present invention may be exemplified, for another example, a peptide prepared by adding 1 to 100 amino acids at the N-terminus or C-terminus of the peptide of the present invention may be exemplified, and for still another example, a peptide prepared by adding 1 to 24 amino acids at the N-terminus or C-terminus of the peptide of the present invention may be exemplified.

The peptide of the present invention may be chemically modified or protected with an organic group at the N-terminus and/or C-terminus, or may be modified by adding amino acids at the peptide terminus in order to protect the peptide from protease in vivo and to increase stability thereof. In particular, since chemically synthesized peptides have charged N-terminus and C-terminus, N-terminal acetylation, N-terminal methylation, or/and C-terminal amidation may be performed, or D-amino acid introduction, peptide bond modification such as $CH_2-NH$, $CH_2-S$, $CH_2-S=0$, $CH_2-CH_2$, backbone modification, or side-chain modification may be included in order to remove the charge, but is not limited thereto. Methods of preparing peptidomimetic compounds are well known in the art, for example, referring to a description in Quantitative Drug Design, C.A. Ramsden Gd., Choplin Pergamon Press (1992).

The term "backbone modification", as used herein, refers to direct modification of amino acids constituting a peptide backbone with amino acid analogs, in which the backbone (main chain) refers to a main chain- or ring-shaped framework of amino acids constituting a peptide. The amino acid analog refers to an amino acid modified by substitution of hydrogen atoms on the nitrogen or a-carbon of the amino acid backbone.

The term "side-chain modification", as used herein, refers to the modification of side-chains of amino acids by using a chemical material, in which the side-chains of amino acids refer to atomic groups branched from a main chain- or ring-shaped framework of amino acids constituting a peptide. Examples of the peptide side-chain modification may include amino group modification such as reductive alkylation; amidation with methyl acetimidate; alkylation with acetic anhydride; carbamylation of amino groups with cyanate; trinitrobenzylation of amino acids with 2,4,6-trinitrobenzene sulfonic acid (TNBS); alkylation of amino groups with succinic anhydride; and pyridoxylation with pyridoxal-5-phosphate followed by reduction with NaBH4.

Further, the peptide of the present invention may be used alone or in combination with various carriers approved as a drug, such as an organic solvent. In order to improve stability and efficacy, the peptide of the present invention may also be used by including carbohydrates such as glucose, sucrose, or dextran, antioxidants such as ascorbic acid or glutathione, chelating agents, low molecular weight proteins, other stabilizers, etc.

Figure 1B:
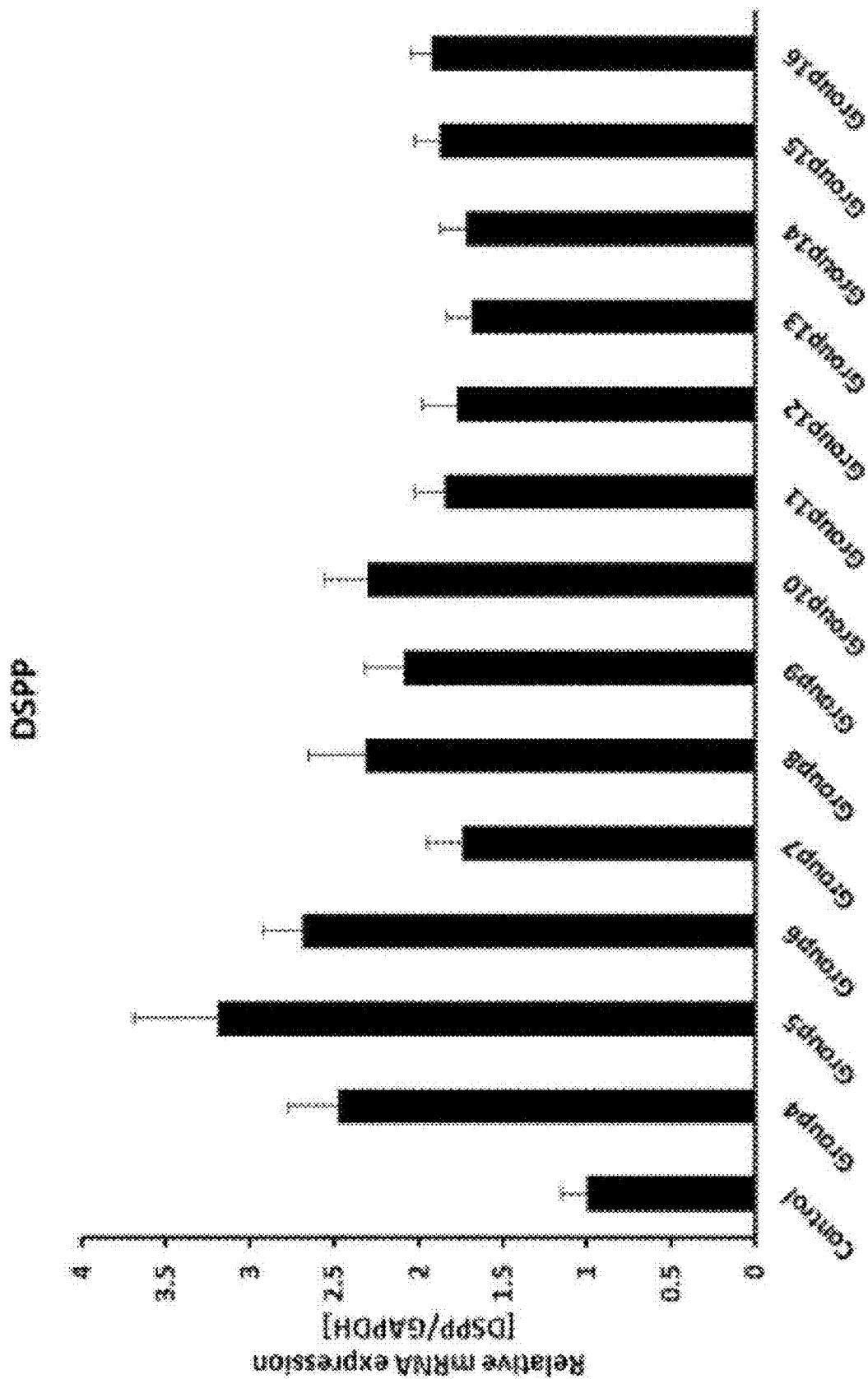
FIG. 1B is another graph showing the result of comparing the expression levels of Dspp, odontoblast differentiation marker gene, in human dental pulp cells (hDPCs) treated with the novel peptide of the present invention.

According to an embodiment of the present invention, 128 kinds of peptides corresponding to Formula 1 of the present invention were synthesized, and effects of the synthesized peptides on an expression level of Dspp gene, which is an odontoblast differentiation marker gene were examined. As a result, it was confirmed that all mRNA levels of the odontoblast differentiation marker Dspp gene in human dental pulp cells which were treated with 128 kinds of the peptides were 8 times higher, 6 times higher, 3 times higher, or at least 1.5 times higher than an mRNA level of the Dspp gene which was measured in human dental pulp cells (control group) which were treated with none of the peptides of the present invention (FIG. 1A, FIG. 1B and Tables 18 to 33).

As reported up to now, it is known that as the mRNA level of DSPP is increased, odontoblast differentiation and dentin regeneration are promoted, and therefore, it can be seen that 128 kinds of the peptides showing the effect of increasing the mRNA level of Dspp gen may exhibit the effect of promoting odontoblast differentiation and dentin regeneration (Taduru Sreenath et al., THE JOURNAL OF BIOLOGICAL CHEMISTRY, Vol. 278, No. 27, Issue of July 4, pp. 24874-24880, 2003; William T. Butler et al., Connective Tissue Research, 44(Suppl. 1): 171-178, 2003).

Figure 2A:
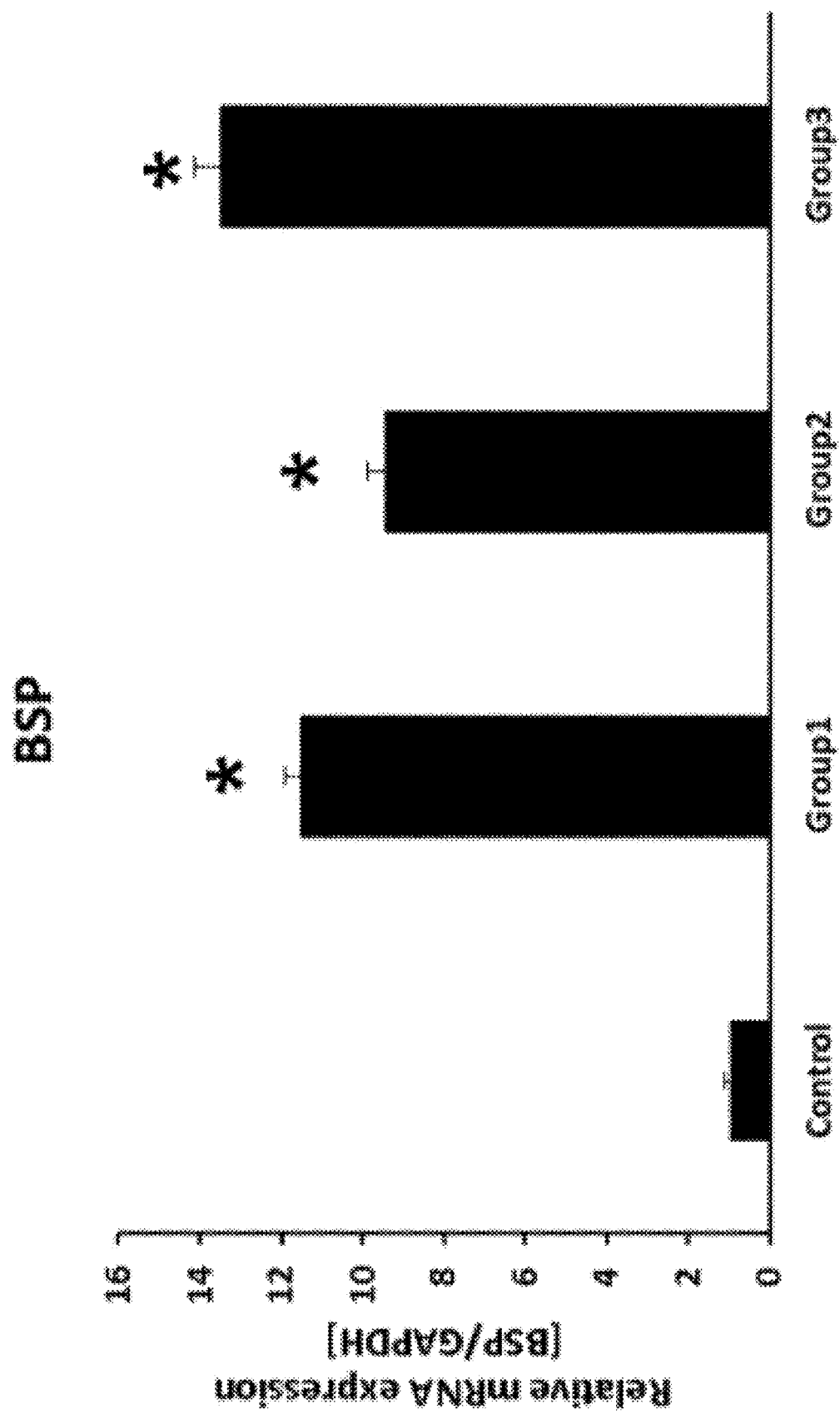
FIG. 2A is a graph showing the results of comparing the expression levels of the BSP, a bone and cementum differentiation marker gene, in human bone marrow-derived mesenchymal stem cells (hBMSCs) treated with the novel peptide of the present invention.

Further, an embodiment of the present invention, the effects of the synthesized peptides on an expression level of BSP gene, which is a differentiation marker gene of osteoblasts/cementoblasts, were examined. As a result, it was confirmed that all mRNA levels of the BSP, osteoblasts/cementoblasts differentiation marker BSP gene in human dental pulp cells which were treated with 128 kinds of the peptides were 13 times higher, 12 times higher, 9 times higher, or at least 3 times higher than an mRNA level of the BSP gene which was measured in human dental pulp cells (control group) which were treated with none of the peptides of the present invention (FIG. 2A, FIG. 2B).

It is known that as the mRNA level of BSP is increased, osteoblasts/cementoblasts differentiation and bone and cementum differentiations are promoted, and therefore, it can be seen that 128 kinds of the peptides showing the effect of increasing the mRNA level of BSP gene may exhibit the effect of promoting osteoblasts/cementoblasts and odontoblast differentiation and dentin regeneration. In another aspect, the present invention provides a polynucleotide encoding the peptide.

The polynucleotide may be modified by substitution, deletion, or insertion of one or more bases, or a combination thereof. When the nucleotide sequence is prepared by chemical synthesis, a synthetic method widely known in the art, for example, a method described in a literature (Engels and Uhlmann, Angew Chem IntEd Engl., 37:73-127, 1988) may be used, and the nucleotide sequence may be synthesized by triester, phosphite, phosphoramidite and H-phosphate methods, PCR and other auto primer methods, oligonucleotide synthesis on solid supports, etc. For example, the polynucleotide encoding the peptide of the present invention may include a nucleotide sequence of SEQ ID NO: 4.

In still another aspect, the present invention provides an expression vector including the polynucleotide, a transformant including the expression vector, and a method of preparing the peptide by using the transformant.

The term "expression vector", as used herein, refers to a recombinant vector capable of expressing a target peptide in a host cell, and refers to a genetic construct including essential regulatory elements which are operably linked to express a gene insert. The expression vector includes expression regulatory sequences such as an initiation codon, a stop codon, a promoter, an operator, etc. The initiation and stop codons are generally considered as part of a nucleotide sequence encoding a polypeptide and are necessary to be functional in an individual to whom a genetic construct has been administered, and must be in frame with the coding sequence. The promoter of the vector may be constitutive or inducible.

The term "operably linked", as used herein, refers to a functional linkage between a nucleic acid expression control sequence and a nucleotide sequence encoding a target protein or RNA in such a manner as to allow general functions. For example, a promoter may be operably linked to a nucleotide sequence encoding a protein or RNA to influence the expression of the coding sequence. The operable linkage to the expression vector may be prepared by using a recombinant genetic technique well known in the art, and site-specific DNA cleavage and ligation may be carried out by using enzymes generally known in the art.

Further, the expression vector may include signal sequences for the discharge of the peptide in order to promote isolation of the peptide from a cell culture. Specific initiation signals may also be required for efficient translation of inserted nucleotide sequences. These signals include ATG initiation codon and adjacent sequences. In some cases, exogenous translational control signals, including ATG initiation codon, should be provided. These exogenous translational control signals and initiation codons may be of a variety of origins, both natural and synthetic. The efficiency of expression may be enhanced by the introduction of appropriate transcription or translation enhancer elements.

In addition, the expression vector may further include a protein tag that may be optionally removed by endopeptidase in order to facilitate the detection of the peptide.

The term "tag", as used herein, refers to a molecule which exhibits a quantifiable activity or characteristic. The tag may include fluorescent molecules including chemical fluorescent such as fluorescein and polypeptide fluorescent such as green fluorescent protein (GFP) or related proteins; and epitope tags such as a Myc tag, a Flag tag, a His-tag, a leucine tag, an IgG tag, a streptavidin tag, etc. In particular, if an epitope tag is used, a peptide tag consisting of preferably 6 or more amino acid residues, and more preferably, about 8 to 50 amino acid residues may be used.

In the present invention, the expression vector may include a nucleotide sequence encoding the above-described peptide for promoting regeneration of hard tissue, including dentin, bone, and cementum and/or dental pulp and treating dentin-dental pulp diseases and/or periodontal diseases of the present invention. The vector used herein is not expressly limited, as long as it can produce the peptide. Preferably, the vector may be plasmid DNA, phage DNA, etc. More preferably, the vector may be a commercially developed plasmid (pUC18, pBAD, pIDTSAMRT-AMP, etc.), an E. coli-derived plasmid (pYG601BR322, pBR325, pUC118, pUC119, etc.), a Bacillus subtilis-derived plasmid (pUB110, pTP5, etc.), a yeast-derived plasmid (YEp13, YEp24, YCp50, etc.), a phage DNA (Charon4A, Charon21A, EMBL3, EMBL4, λgt10, λgt11, λZAP, etc.), an animal virus vector (retrovirus, adenovirus, vaccinia virus, etc.), an insect virus (baculovirus, etc.), or the like. For the expression vector, a host cell most suitable for the intended use is preferably selected and used, because the expression level and modification of protein vary depending on the kind of host cell.

The transformant of the present invention may be prepared by transformation of a host with the expression vector of the present invention, and the transformant may express the polynucleotide in the expression vector, thereby producing the peptide. Various methods may perform the transformation. The transformation method is not particularly limited, as long as it may produce the peptide. CaCl2 precipitation, a Hanahan method that is an improved CaCl2 precipitation method by using DMSO (dimethyl sulfoxide) as a reducing agent, electroporation, calcium phosphate precipitation, protoplast fusion, agitation using silicon carbide fiber, Agrobacterium-mediated transformation, PEG-mediated transformation, dextran sulfate-, lipofectamine- or desiccation/inhibition-mediated transformation, etc. may be used. The host used in the preparation of the transformant is not particularly limited, as long as it may produce the peptide of the present invention. The host may be bacterial cells such as *E. coli, Streptomyces, Salmonella typhimurium*, etc.; yeast cells such as *Saccharomyces cerevisiae, Schizosaccharomyces pombe*, etc.; fungal cells such as *Pichia pastoris*, etc.; insect cells such as *Drosophila, Spodoptera* Sf9 cells, etc.; animal cells such as CHO, COS, NSO, 293, Bowes melanoma cells, etc.; and plant cells.

The transformant may be used in a method of producing the peptide for promoting regeneration of hard tissue, including dentin, bone, and cementum and/or dental pulp and treating dentin-dental pulp diseases and/or periodontal diseases of the present invention. Specifically, the method of producing the peptide for promoting regeneration of dentin or dental pulp and treating dentin or dental pulp diseases of the present invention may include (a) culturing the transformant to obtain a culture; and (b) recovering the peptide of the present invention from the culture.

The term "culturing", as used herein, refers to a method of allowing a microorganism to grow under artificially controlled environmental conditions. In the present invention, the method of culturing the transformant may be performed by a method widely known in the art. Specifically, the culturing is not particularly limited, as long as it may express and produce the peptide for promoting regeneration of hard tissue including dentin, bone, and cementum and/or dental pulp and treating dentin or dentin-dental pulp diseases and/or periodontal diseases of the present invention, and the culturing may be performed by a batch process, a fed-batch process, or a repeated fed-batch process.

A medium used in the culturing includes appropriate carbon sources, nitrogen sources, amino acids, vitamins, etc. and should satisfy the requirements of a specific strain suitably while adjusting temperature, pH, etc. under aerobic conditions. Applicable carbon sources may include, in addition to mixed sugars of glucose and xylose as a primary carbon source, sugars and carbohydrates such as sucrose, lactose, fructose, maltose, starch, and cellulose, oils and fats such as soybean oil, sunflower oil, castor oil, coconut oil, etc., fatty acids such as palmitic acid, stearic acid, or linoleic acid, alcohols such as glycerol or ethanol, and organic acids such as acetic acid.

These substances may be used alone or in combination. Applicable nitrogen sources may include inorganic nitrogen sources such as ammonia, ammonium sulfate, ammonium chloride, ammonium acetate, ammonium phosphate, ammonium carbonate, or ammonium nitrate; amino acids such as glutamic acid, methionine, or glutamine; and organic nitrogen sources such as peptone, NZ-amine, meat extract, yeast extract, malt extract, steep corn liquor, casein hydrolysate, fish meal or digested products thereof, defatted soybean cake or digested products thereof, etc. These nitrogen sources may be used alone or in combination. The medium may include, as phosphorus sources, potassium phosphate monobasic, potassium phosphate dibasic, and corresponding sodium-containing salts. Applicable phosphorus sources may include potassium dihydrogen phosphate, dipotassium hydrogen phosphate, or corresponding sodium-containing salts. Also, inorganic compounds may include sodium chloride, calcium chloride, iron chloride, magnesium sulfate, iron sulfate, manganese sulfate, and calcium carbonate. In addition to the above materials, essential growth materials such as amino acids and vitamins may be used.

Further, appropriate precursors may be used in the culture medium. During culturing, the above-described materials may be appropriately added to the culture in a batch, fed-batch, or continuous manner, but are not limited thereto. The pH of the culture may be adjusted by appropriately using a basic compound such as sodium hydroxide, potassium hydroxide, or ammonia, or an acidic compound such as phosphoric acid or sulfuric acid.

In addition, the formation of bubbles may be inhibited by using an antifoaming agent such as fatty acid polyglycol ester. In order to maintain an aerobic state, oxygen or oxygen-containing gas (e.g., air) may be injected into the culture. The temperature of the culture is generally 27° C. to 37° C., preferably 30° C. to 35° C. Culturing is continued until the desired level of the peptide production will be obtained. This is achieved within 10 hours to 100 hours.

In addition, the recovering of the peptide from the culture may be performed by a method known in the art. Specifically, the recovering method is not particularly limited, as long as it may recover the produced peptide. Preferably, a method such as centrifugation, filtration, extraction, spraying, drying, evaporation, precipitation, crystallization, electrophoresis, fractional dissolution (e.g., ammonium sulfate precipitation), chromatography (e.g., ion exchange, affinity, hydrophobic, and size exclusion), etc. may be used.

In still another aspect, the present invention provides a pharmaceutical composition for preventing or treating dentin-dental pulp diseases and/or periodontal diseases comprising the peptide.

As described above, when the peptide for promoting regeneration of hard tissue including dentin, bone and cementum and/or dental pulp and treating dentin-dental pulp diseases and/or periodontal diseases of the present invention is transplanted into the body, together with human dental pulp cells, formation of dentin/dental pulp-like tissue by the human dental pulp cells may be promoted, and when the peptide is applied to the damaged dentin or dental pulp site, the same physiologic dentin as observed in the natural human tooth dentin may be formed. Therefore, the peptide may be used as an active ingredient of the pharmaceutical composition for treating dentin-dental pulp diseases, which are caused by damage to dentin or dental pulp.

The peptide included in the pharmaceutical composition may be used in a single form of the peptide or in a polypeptide form of 2 or more repeats of the peptide, and the peptide may also be used in a complex form of a drug having a therapeutic effect on dentin or dental pulp diseases linked at the N-terminus or C-terminus of the peptide.

The term "dentin-dental pulp diseases", as used herein, refer to all diseases caused by damaged dental pulp tissue and dentin linked to the dental pulp due to damage to the dentin and dental pulp tissues.

In the present invention, the dentin-dental pulp diseases are not particularly limited, as long as the peptide of the present invention exhibits the therapeutic effects on the diseases, and the dentin or dental pulp diseases may include, for example, dentin hypersensitivity, pulp hyperemia, pulpitis, pulp degeneration, pulp necrosis, gangrenous pulp, etc.

In still another aspect, the present invention provides a pharmaceutical composition for preventing or treating periodontal diseases comprising the peptide. As described above, when the peptide for promoting regeneration of hard tissue including dentin, bone and cementum and/or dental pulp and treating dentin-dental pulp diseases and/or periodontal diseases of the present invention is transplanted into the body, together with human dental pulp cells, formation of bone-like tissue by the human dental pulp cells may be promoted. Therefore, the peptide may be used as an active ingredient of the pharmaceutical composition for treating periodontal diseases, which are caused by damage to bone and/or cementum.

The peptide included in the pharmaceutical composition may be used in a single form of the peptide or in a polypeptide form of 2 or more repeats of the peptide, and the peptide may also be used in a complex form of a drug having a therapeutic effect on dentin or dental pulp diseases linked at the N-terminus or C-terminus of the peptide.

The term "periodontal disease", as used herein, also referred to as chronic periodontitis, refers to a disease that infects the periodontal ligament and adjacent tissues by infection of bacteria in the gap between the gingiva and the teeth, depending on the severity of the disease it is divided into gingivitis or periodontitis. During the onset of periodontal disease, inflammation progresses, and more tissues are damaged to form a periodontal pocket. It is known when periodontitis gets worse, and the periodontal pocket becomes deeper the periodontal pocket causes inflammation of periodontal ligament and finally cause bone loss.

In the present invention, the periodontal diseases are not particularly limited, as long as the peptide of the present invention exhibits the therapeutic effects on the diseases, and the dentin or dental pulp diseases may include, for example, gingivitis, periodontitis, periodontal pocket or periodontal abscess, etc.

The term "preventing", as used herein, means all actions by which the occurrence of dentin-dental pulp diseases is restrained or retarded by administration of the pharmaceutical composition for preventing or treating dentin-dental pulp diseases including the peptide of the present invention.

The term "treating", as used herein, means all actions by which dentin dental pulp diseases are treated by promoting regeneration of dentin or dental pulp by administering the pharmaceutical composition comprising the peptide of the present invention as an active ingredient to a subject in need of treatment of dentin-dental pulp diseases or all actions which are carried out by administering a pharmaceutical composition comprising the peptide of the present invention as an active ingredient to an individual in need of treatment of periodontal disease by promoting regeneration of bone and/or cementum.

The pharmaceutical composition of the present invention may be prepared in the form of a pharmaceutical composition for treating dentin-dental pulp diseases and/or periodontal diseases further including, in addition to the peptide, an appropriate carrier (natural or non-natural carrier), excipient, or diluent commonly used in the preparation of pharmaceutical compositions. Notably, the pharmaceutical composition may be formulated according to a standard method in the form of a sterile injectable solution that may be administered to dentin or dentin-dental pulp diseases and/or periodontal diseases-induced site. In the present invention, the carrier, excipient, and diluent which may be included in the pharmaceutical composition may include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methyl hydroxybenzoate, propyl hydroxybenzoate, talc, magnesium stearate, mineral oils, collagen, etc. Upon formulation, commonly used diluents or excipients such as a filler, an extender, a binder, a wetting agent, a disintegrant, a surfactant, etc. may be used. In particular, a sterilized aqueous solution, a non-aqueous solvent, a suspension, an emulsion, a freeze-dried preparation, a suppository, an ointment (e.g., pulp liner, etc.) may be included. As non-aqueous solvents or suspensions, propylene glycol, polyethylene glycol, plant oils such as olive oil, injectable esters such as ethyl oleate, etc. may be used. As a base of the suppositories, witepsol, Macrogol, Tween 61, cacao butter, laurin fat, glycerogelatin, etc. may be used.

A content of the peptide in the pharmaceutical composition of the present invention is not particularly limited, but the peptide may be included in an amount of 0.0001% by weight to 50% by weight, more preferably, 0.01% by weight to 20% by weight, based on the total eight of the final composition.

The pharmaceutical composition of the present invention may be administered in a pharmaceutically effective amount. The term "pharmaceutically effective amount", as used herein, refers to an amount sufficient to treat or prevent diseases, at a reasonable benefit/risk ratio applicable to any medical treatment or prevention. An effective dosage level may be determined depending on factors including the severity of the disease, drug activity, a patient's age, body weight, health conditions, sex, sensitivity to the drug, administration time, administration route, and excretion rate of the composition of the present invention, duration of treatment, drugs blended with or co-administered with the composition of the present invention, and other factors known in the medical field. The pharmaceutical composition of the present invention may be administered individually or in combination with a known pharmaceutical composition for treating dentin-dental pulp diseases and/or periodontal diseases. It is essential to administer the composition in a minimum amount that may exhibit a maximum effect without causing side effects, because of all the above-described factors.

An administration dose of the pharmaceutical composition of the present invention may be determined by those skilled in the art, because of the purpose of use, severity of the disease, a patient's age, body weight, sex, and medical history, a kind of a material used as an active ingredient, etc. For example, the pharmaceutical composition of the present invention may be administered at a dose of about 0.1 ng/kg to about 100 mg/kg. Preferably, about 1 ng/kg to about 10 mg/kg per adult and administration frequency of the composition of the present invention is not particularly limited. However, the composition may be administered once a day or several times a day in divided doses. The administration dose does not limit the scope of the present invention in any aspect.

In still another aspect, the present invention provides a method of treating dentin-dental pulp diseases, the method including administering the pharmaceutically effective amount of the pharmaceutical composition to a human or a subject having dentin-dental pulp diseases, excluding humans.

The term "subject, as used herein, may include mammals including humans, rats, livestock, etc. in need of treatment of dentin-dental pulp diseases and/or periodontal diseases without limitation, but humans can be excluded from the subjects having the above diseases.

The pharmaceutical composition for treating dentin-dental pulp diseases and/or periodontal diseases of the present invention may be administered via any general route, as long as the pharmaceutical composition is able to reach a target tissue.

The pharmaceutical composition may be administered, but is not particularly limited to, via intraoral administration, intraoral injection, etc., depending on the purpose.

In still another aspect, the present invention provides a quasi-drug composition for preventing or alleviating dentin-dental pulp diseases, including the peptide.

The term "alleviating", as used herein, means all actions that at least reduce a parameter related to the conditions to be treated, for example, the degree of symptom.

In the present invention, the alleviating is to be interpreted as all actions by which symptoms of dentin-dental pulp diseases have taken a turn for the better or been modified favorably by promoting regeneration of dentin-dental pulp or symptoms of periodontal diseases have taken a turn for the better or been modified favorably by promoting regeneration of bone and/or cementum by administering the pharmaceutical composition including the peptide of the present invention as an active ingredient to a subject in need of treatment of dentin or dental pulp diseases.

The term "quasi-drug", as used herein, refers to an article having a milder action than drugs, among articles being used for diagnosis, treatment, improvement, alleviation, handling, or prevention of human or animal diseases. For example, according to Pharmaceutical Affairs Law, the quasi-drugs are those, excluding articles used as drugs, including articles made from fiber or rubber which are used to treat or prevent human or animal diseases, articles, other than a tool or a machine, or an analog thereof, which have a mild action on or have no direct influence on the human body, and articles which are used for disinfection or pest control for the prevention of infectious diseases.

In the present invention, a kind of formulation of the quasi-drug composition including the peptide is not particularly limited, but the quasi-drug composition may be, for example, oral antiseptic mouthwashes, oral hygiene products, toothpastes, floss, oral ointments, etc.

In still another aspect, the present invention provides a health functional food composition for preventing or alleviating dentin-dental pulp diseases and/or periodontal diseases, including the peptide.

The term "food", as used herein, includes meats, sausages, breads, chocolates, candies, snacks, confectionery, pizzas, ramen noodles, other noodles, gums, dairy products including ice-creams, various soups, beverages, teas, drinks, alcoholic beverages, and vitamin complexes, health functional foods, health foods, etc., and the food includes all foods in the ordinary acceptation of the term.

The term "functional food", as used herein, is the term identical to the food for special health use (FoSHU), and refers to a food having high medical, medicinal effects, which is processed to exhibit the biologically modulating function efficiently as well as to supply nutrients. Here, the term "functional" indicates a beneficial effect for human health, such as the regulation of nutrients for the structure and function of the human body, physiological action, etc. The food of the present invention may be prepared according to a method commonly employed in the art, and raw materials and ingredients commonly used in the art may be added upon preparing the food. In addition, a formulation of the food is not limited, as long as the formulation is accepted as a food. The food composition of the present invention may be prepared as a variety of formulations. Since the food is used as raw materials, unlike general drugs, the food composition lacks side effects which may occur when a drug is taken for a long period, and may have excellent portability. Therefore, the food of the present invention may be taken as a supplement for enhancing the effects of preventing or alleviating dentin-dental pulp diseases and/or periodontal diseases.

The health food means food is having effects of actively maintaining or promoting health conditions, as compared with general foods, and the health supplement food means a food for supplementing health. If necessary, the health functional food, health food, and health supplement food may be interchangeably used.

Specifically, the health functional food is a food prepared by adding the peptide of the present invention to food materials such as beverages, teas, spices, gums, confectionery, etc., or prepared as a capsule, a powder, a suspension, etc. The functional health food means that it takes a specific effect on health when consumed, but unlike general drugs, the health functional food has an advantage of having no side effects that may occur when a drug is taken for a long time, because it uses a food as a raw material.

Since the food composition of the present invention is routinely ingested, the food composition is expected to show high efficacy on prevention or improvement of dentin-dental pulp diseases and/or periodontal diseases. Thus, it may be very usefully applied.

The food composition may further include a physiologically acceptable carrier. A kind of the carrier is not particularly limited. Any carrier may be used, as long as it is commonly used in the art.

Further, the food composition may include additional ingredients that are commonly used in food compositions to improve smell, taste, vision, etc. For example, the food composition may include vitamins A, C, D, E, B1, B2, B6, B12, niacin, biotin, folate, pantothenic acid, etc. Additionally, the food composition may also include minerals such as Zn, Fe, Ca, Cr, Mg, Mn, Cu, etc. Additionally, the food composition may also include amino acids such as lysine, tryptophan, cysteine, valine, etc. Additionally, the food composition may also include food additives, such as preservatives (potassium sorbate, sodium benzoate, salicylic acid, sodium dehydroacetate, etc.), disinfectants (bleaching powder, higher bleaching powder, sodium hypochlorite, etc.), antioxidants (butyl hydroxyanisole (BHA), butylhydroxytoluene (BHT), etc.), coloring agents (tar color, etc.), color-developing agents (sodium nitrite, etc.), bleaching agents (sodium sulfite), seasonings (monosodium glutamate (MSG), etc.), sweeteners (dulcin, cyclamate, saccharin, sodium, etc.), flavors (vanillin, lactones, etc.), swelling agents (alum, potassium D-bitartrate, etc.), fortifiers, emulsifiers, thickeners (adhesive pastes), film-forming agents, gum base agents, antifoaming agents, solvents, improvers, etc. The additives may be selected and used in an appropriate amount according to the food types.

The peptide of the present invention may be added as it is, or may be used in conjunction with other foods or food ingredients according to a standard method, or may be used appropriately according to a standard method. Mixing amounts of the active ingredient may be suitably determined depending upon the purpose of use (prophylactic, health or therapeutic treatment). Generally, upon production of a food or a beverage, the food composition of the present invention may be added in an amount of 50 parts by weight or less, specifically 20 parts by weight or less, based on the total weight of the food or the beverage. However, when prolonged intake is intended for health and hygiene, the food composition may be included in an amount below the above range. In addition, since there is no safety problem, the active ingredient may be used in an amount above the high range.

The food composition of the present invention may be used as, for example, a health beverage composition. In this case, the health beverage composition may further include various flavors or natural carbohydrates, as in common beverages. The natural carbohydrates may include monosaccharides such as glucose and fructose; disaccharides such as maltose and sucrose; polysaccharides such as dextrin and cyclodextrin; and sugar alcohols such as xylitol, sorbitol, and erythritol. The sweeteners may be natural sweeteners such as thaumatin or a stevia extract; or synthetic sweeteners such as saccharine or aspartame. The natural carbohydrate may be generally used in an amount of about 0.01 g to 0.04 g, and specifically, about 0.02 g to 0.03 g, based on 100 mL of the health beverage composition of the present invention.

In addition, the health beverage composition may include various nutrients, vitamins, minerals, flavors, colorants, pectic acid and salts thereof, alginic acid and salts thereof, organic acids, protective colloidal thickeners, pH modifiers, stabilizers, antiseptics, glycerin, alcohols, carbonating agents, etc. Moreover, the health beverage composition may include the fruit flesh used to prepare natural fruit juices, fruit juice beverages, or vegetable beverages. These ingredients may be used individually or in combination. A proportion of the additives is not critical, but is generally selected from 0.01 parts by weight to 0.1 parts by weight per 100 parts by weight of the health beverage composition of the present invention.

The food composition of the present invention may include the peptide of the present invention in a variety of % by weight, as long as it may exhibit the effect of preventing or alleviating dentin-dental pulp diseases and/or periodontal diseases. Specifically, the peptide of the present invention may be included in an amount of 0.00001% by weight to 100% by weight or 0.01% by weight to 80% by weight, based on the total weight of the food composition, but is not limited thereto.

In still another aspect, the present invention provides a method of preventing or treating dentin-dental pulp diseases and/or periodontal diseases, the method including administering the composition, including the peptide to a subject.

In still another aspect, the present invention provides a method of promoting regeneration of dentin or dental pulp tissues and/or hard tissue including dentin, bone, and cementum, the method including administering the composition including the peptide to a subject.

In still another aspect, the present invention provides use of a peptide including an amino acid sequence of the following Formula 1 or a composition comprising the peptide in promoting regeneration of hard tissue including dentin, bone and cementum and/or dental pulp and treating dentin-dental pulp diseases or periodontal diseases:

K-Y-R1-R2-R3-R4-R5         (Formula 1)

wherein R1 and R2 are arginine(R), lysine(K), glutamine (Q) or asparagine(N), respectively;

R3, R4, and R5 are arginine(R) or lysine(K), respectively.

In still another aspect, the present invention provides use of a peptide including any one amino acid sequence of SEQ ID NOS: 1 to 128 or a composition including the peptide in promoting regeneration of hard tissue including dentin, bone and cementum and/or dental pulp and in treating dentin-dental pulp diseases and/or periodontal diseases.

Hereinafter, the present invention will be described in more detail with reference to Examples. However, these examples are for illustrative purposes only, and the scope of the present invention is not intended to be limited by these Examples.

EXAMPLE 1

Methods and Materials

Synthesis of peptides for promoting generation of hard tissue including dentin, bone and cementum and/or dental pulp and in treating dentin-dental pulp diseases and/or periodontal diseases The present inventors synthesized a peptide (SEQ ID NO: 1) showing the effect of promoting regeneration of hard tissue including dentin, bone and cementum and/or dental pulp tissue by a 9-fluorenylmethyloxycarbonyl (Fmoc) method, and they synthesized peptides of Representative groups (Tables 1 to 16) by substituting the amino acids of the synthesized peptide.

```
                                        (SEQ ID NO: 1)
                    N-KYQRRKK-C
```

First, peptides of Group 1 were synthesized by using the peptide of SEQ ID NO: 1 or by substituting any amino acid at positions 5 to 7 of the peptide of SEQ ID NO: 1 with lysine or arginine (Table 1).

TABLE 1

| Peptides of Group 1 | |
|---|---|
| SEQ ID NO: | Amino acid sequence (N-C) |
| 1 | KYQRRKK |
| 2 | KYQRRKR |
| 3 | KYQRRRK |
| 4 | KYQRRRR |
| 5 | KYQRKKK |
| 6 | KYQRKRK |
| 7 | KYQRKKR |
| 8 | KYQRKRR |

Next, peptides of Group 2 were synthesized by substituting an amino acid at position 3 of the peptide of SEQ ID NO: 1 with arginine, by substituting an amino acid at position 4 of the peptide of SEQ ID NO: 1 with glutamine, or by substituting any amino acid at positions 5 to 7 of the peptide of SEQ ID NO: 1 with lysine or arginine (Table 2).

TABLE 2

Peptides of Group 2

| SEQ ID NO: | Amino acid sequence (N-C) |
|---|---|
| 9 | KYRQRKK |
| 10 | KYRQRKR |
| 11 | KYRQRRK |
| 12 | KYRQRRR |
| 13 | KYRQKKK |
| 14 | KYRQKRK |
| 15 | KYRQKKR |
| 16 | KYRQKRR |

Next, peptides of Group 3 were synthesized by substituting an amino acid at position 3 of the peptide of SEQ ID NO: 1 with lysine, by substituting an amino acid at position 4 of the peptide of SEQ ID NO: 1 with glutamine, or by substituting any amino acid at positions 5 to 7 of the peptide of SEQ ID NO: 1 with lysine or arginine (Table 3).

TABLE 3

Peptides of Group 3

| SEQ ID NO: | Amino acid sequence (N-C) |
|---|---|
| 17 | KYKQRKK |
| 18 | KYKQRKR |
| 19 | KYKQRRK |
| 20 | KYKQRRR |
| 21 | KYKQKKK |
| 22 | KYKQKRK |
| 23 | KYKQKKR |
| 24 | KYKQKRR |

Next, peptides of Group 4 were synthesized by substituting an amino acid at position 4 of the peptide of SEQ ID NO: 1 with glutamine, or by substituting any amino acid at positions 5 to 7 of the peptide of SEQ ID NO: 1 with lysine or arginine (Table 4).

TABLE 4

Peptides of Group 4

| SEQ ID NO: | Amino acid sequence (N-C) |
|---|---|
| 25 | KYQQRKK |
| 26 | KYQQRKR |
| 27 | KYQQRRK |
| 28 | KYQQRRR |
| 29 | KYQQKKK |
| 30 | KYQQKRK |
| 31 | KYQQKKR |
| 32 | KYQQKRR |

Next, peptides of Group 5 were synthesized by substituting an amino acid at position 3 of the peptide of SEQ ID NO: 1 with arginine, or by substituting any amino acid at positions 5 to 7 of the peptide of SEQ ID NO: 1 with lysine or arginine (Table 5).

TABLE 5

Peptides of Group 5

| SEQ ID NO: | Amino acid sequence (N-C) |
|---|---|
| 33 | KYRRRKK |
| 34 | KYRRRKR |
| 35 | KYRRRRK |
| 36 | KYRRRRR |
| 37 | KYRRKKK |
| 38 | KYRRKRK |
| 39 | KYRRKKR |
| 40 | KYRRKRR |

Next, peptides of Group 6 were synthesized by substituting an amino acid at position 3 of the peptide of SEQ ID NO: 1 with lysine, by substituting any amino acid at positions 5 to 7 of the peptide of SEQ ID NO: 1 with lysine or arginine (Table 6).

TABLE 6

Peptides of Group 6

| SEQ ID NO: | Amino acid sequence (N-C) |
|---|---|
| 41 | KYKRRKK |
| 42 | KYKRRKR |
| 43 | KYKRRRK |
| 44 | KYKRRRR |
| 45 | KYKRKKK |
| 46 | KYKRKRK |
| 47 | KYKRKKR |
| 48 | KYKRKRR |

Next, peptides of Group 7 were synthesized by substituting an amino acid at position 4 of the peptide of SEQ ID NO: 1 with lysine, or by substituting any amino acid at positions 5 to 7 of the peptide of SEQ ID NO: 1 with lysine or arginine (Table 7).

TABLE 7

Peptides of Group 7

| SEQ ID NO: | Amino acid sequence (N-C) |
|---|---|
| 49 | KYQKRKK |
| 50 | KYQKRKR |
| 51 | KYQKRRK |
| 52 | KYQKRRR |
| 53 | KYQKKKK |
| 54 | KYQKKRK |
| 55 | KYQKKKR |
| 56 | KYQKKRR |

Next, peptides of Group 8 were synthesized by substituting an amino acid at position 3 of the peptide of SEQ ID NO: 1 with asparagine, by substituting an amino acid at position 4 of the peptide of SEQ ID NO: 1 with lysine, or by substituting any amino acid at positions 5 to 7 of the peptide of SEQ ID NO: 1 with lysine or arginine (Table 8).

TABLE 8

Peptides of Group 8

| SEQ ID NO: | Amino acid sequence (N-C) |
|---|---|
| 57 | KYNKRKK |
| 58 | KYNKRKR |
| 59 | KYNKRRK |
| 60 | KYNKRRR |
| 61 | KYNKKKK |
| 62 | KYNKKRK |
| 63 | KYNKKKR |
| 64 | KYNKKRR |

Next, peptides of Group 9 were synthesized by substituting an amino acid at position 3 of the peptide of SEQ ID NO: 1 with asparagine, by substituting any amino acid at positions 5 to 7 of the peptide of SEQ ID NO: 1 with lysine or arginine (Table 9).

TABLE 9

Peptides of Group 9

| SEQ ID NO: | Amino acid sequence (N-C) |
|---|---|
| 65 | KYNRRKK |
| 66 | KYNRRKR |
| 67 | KYNRRRK |
| 68 | KYNRRRR |
| 69 | KYNRKKK |
| 70 | KYNRKRK |
| 71 | KYNRKKR |
| 72 | KYNRKRR |

Next, peptides of Group 10 were synthesized by substituting an amino acid at position 3 of the peptide of SEQ ID NO: 1 with arginine, by substituting an amino acid at position 4 of the peptide of SEQ ID NO: 1 with asparagine, or by substituting any amino acid at positions 5 to 7 of the peptide of SEQ ID NO: 1 with lysine or arginine (Table 10).

TABLE 10

Peptides of Group 10

| SEQ ID NO: | Amino acid sequence (N-C) |
|---|---|
| 73 | KYRNRKK |
| 74 | KYRNRKR |
| 75 | KYRNRRK |
| 76 | KYRNRRR |
| 77 | KYRNKKK |
| 78 | KYRNKRK |
| 79 | KYRNKKR |
| 80 | KYRNKRR |

Next, peptides of Group 11 were synthesized by substituting an amino acid at position 3 of the peptide of SEQ ID NO: 1 with lysine, by substituting an amino acid at position 4 of the peptide of SEQ ID NO: 1 with asparagine, or by substituting any amino acid at positions 5 to 7 of the peptide of SEQ ID NO: 1 with lysine or arginine (Table 11).

TABLE 11

Peptides of Group 11

| SEQ ID NO: | Amino acid sequence (N-C) |
|---|---|
| 81 | KYKNRKK |
| 82 | KYKNRKR |
| 83 | KYKNRRK |
| 84 | KYKNRRR |
| 85 | KYKNKKK |
| 86 | KYKNKRK |
| 87 | KYKNKKR |
| 88 | KYKNKRR |

Next, peptides of Group 12 were synthesized by substituting an amino acid at position 4 of the peptide of SEQ ID NO: 1 with asparagine, or by substituting any amino acid at positions 5 to 7 of the peptide of SEQ ID NO: 1 with lysine or arginine (Table 12).

TABLE 12

Peptides of Group 12

| SEQ ID NO: | Amino acid sequence (N-C) |
|---|---|
| 89 | KYQNRKK |
| 90 | KYQNRKR |
| 91 | KYQNRRK |
| 92 | KYQNRRR |
| 93 | KYQNKKK |
| 94 | KYQNKRK |
| 95 | KYQNKKR |
| 96 | KYQNKRR |

Next, peptides of Group 13 were synthesized by substituting an amino acid at position 3 of the peptide of SEQ ID NO: 1 with asparagine, by substituting an amino acid at position 4 of the peptide of SEQ ID NO: 1 with glutamine, or by substituting any amino acid at positions 5 to 7 of the peptide of SEQ ID NO: 1 with lysine or arginine (Table 13).

TABLE 13

Peptides of Group 13

| SEQ ID NO: | Amino acid sequence (N-C) |
|---|---|
| 97 | KYNQRKK |
| 98 | KYNQRKR |
| 99 | KYNQRRK |
| 100 | KYNQRRR |
| 101 | KYNQKKK |
| 102 | KYNQKRK |
| 103 | KYNQKKR |
| 104 | KYNQKRR |

Next, peptides of Group 2 were synthesized by substituting an amino acid at positions 3 and 4 of the peptide of SEQ ID NO:
1 with asparagine, by substituting any amino acid at positions 5 to 7 of the peptide of SEQ ID NO: 1 with lysine or arginine (Table 14).

TABLE 14

Peptides of Group 14

| SEQ ID NO: | Amino acid sequence (N-C) |
|---|---|
| 105 | KYNNRKK |
| 106 | KYNNRKR |
| 107 | KYNNRRK |
| 108 | KYNNRRR |
| 109 | KYNNKKK |
| 110 | KYNNKRK |
| 111 | KYNNKKR |
| 112 | KYNNKRR |

Next, peptides of Group 15 were synthesized by substituting an amino acid at position 3 of the peptide of SEQ ID NO: 1 with arginine, by substituting an amino acid at position 4 of the peptide of SEQ ID NO: 1 with lysine, or by substituting any amino acid at positions 5 to 7 of the peptide of SEQ ID NO: 1 with lysine or arginine (Table 15).

TABLE 15

Peptides of Group 15

| SEQ ID NO: | Amino acid sequence (N-C) |
|---|---|
| 113 | KYRKRKK |
| 114 | KYRKRKR |
| 115 | KYRKRRK |
| 116 | KYRKRRR |
| 117 | KYRKKKK |
| 118 | KYRKKRK |
| 119 | KYRKKKR |
| 120 | KYRKKRR |

Lastly, peptides of Group 16 were synthesized by substituting an amino acid at positions 3 and 4 of the peptide of SEQ ID NO: 1 with lysine, by substituting any amino acid at positions 5 to 7 of the peptide of SEQ ID NO: 1 with lysine or arginine (Table 16).

TABLE 16

Peptides of Group 16

| SEQ ID NO: | Amino acid sequence (N-C) |
|---|---|
| 121 | KYKKRKK |
| 122 | KYKKRKR |
| 123 | KYKKRRK |
| 124 | KYKKRRR |
| 125 | KYKKKKK |
| 126 | KYKKKRK |
| 127 | KYKKKKR |
| 128 | KYKKKRR |

EXAMPLE 1-2

Cell Culture

Cells were cultured in humidified air containing about 37% of $CO_2$ at 37 ° C. Moreover, they were used in the experiment. Human bone marrow mesenchymal stem cells (hBMSCs) were purchased and used from Lonza (LONZA, Switzerland). hBMSCs were cultured in an alpha-MEM(α-MEM) (Invitrogen) culture medium containing 10% heat-inactivated bovine serum.

EXAMPLE 1-3

Separation and Culture of Human-Derived Dental Pulp Cells

Human dental pulp cells were separated from wisdom teeth of adults (aged 18-22) at the School of Dentistry, Seoul National University. In detail, all experiments were performed after the approval of the Institutional Review Board and the informed consent from patients. Wisdom teeth were fractured according to a method of Jung HS et al. (J Mol Histol.(2011)) to expose the dental pulps, and dental pulp tissues were separated with forceps. Each of the separated dental pulp tissues was cut into small pieces with a razor blade, put in a 60-mm dish, covered with a coverslip, and then cultured in a Dulbecco's modified Eagle's medium. It has been known that human dental pulp cells can differentiate into odontoblast, osteoblast, cementoblast, and periodontal ligament cells under various conditions (Tissue Eng Part A. 2014 April; 20 (7-8): 1342-51).

EXAMPLE 1-4

Analysis of Reverse Transcription-Polymerase Chain Reaction (RT-PCR) and Real-Time PCR Total RNA was extracted from human dental pulp cells (hDPCs), and human bone marrow mesenchymal stem cells (hBMSCs) with TRIzol reagent. 2 μg of the total RNA, 1 μl of reverse transcriptase, and 0.5 μg of oligo (oligo; dT) were used to synthesize cDNA. The synthesized cDNA was used in a real-time polymerase chain reaction. The real-time polymerase chain reaction was performed on an ABI PRISM 7500 sequence detection system (Applied Biosystems) and an SYBR GREEN PCR Master Mix (Takara, Japan). The real-time polymerase chain reaction was performed under conditions of 94° C., 1 min; 95° C., 15 sec; 60° C., 34 sec for 40 cycles. Results were analyzed by a comparative cycle threshold (CT) method. And the used primers are as follows (Table 17).

TABLE 17

| <Complete lists of human real-time PCR primers> | | |
|---|---|---|
| Gene | | Primer (5'-3') |
| hDspp | Forward | CAACCATAGAGAAAGCAAACGCG (SEQ ID NO: 129) |
|  | Reverse | TTTCTGTTGCCACTGCTGGGAC (SEQ ID NO: 130) |
| hNestin | forward | AGCCCTGACCACTCCAGTTTAG (SEQ ID NO: 131) |
|  | reverse | CCCTCTATGGCTGTTTCTTTCTCT (SEQ ID NO: 132) |
| hBSP | forward | GAATGGCCTGTGCTTTCTCAA (SEQ ID NO: 133) |
|  | reverse | TCGGATGAGTCACTACTGCCC (SEQ ID NO: 134) |
| hGAPDH | forward | CCATGGAGAAGGCTGGGG (SEQ ID NO: 135) |
|  | reverse | CAAAGTTCTCATGGATGACC (SEQ ID NO: 136) |

EXAMPLE 1-5

In Vivo Transplantation and Histomorphological Analysis

Human dental pulp cells (hDPCs) were isolated and used for in vivo transplantation experiments. Human dental pulp cells ($2 \times 10^6$) were mixed with 100 mg of hydroxy apatite/tricalcium phosphate (HA/TCP) ceramic powder (Zimmer, USA) alone, or with the peptide of the invention (10 μg) with 0.5% fibrin gel respectively, and then the prepared implant transplanted to a mice with compromised immune systems (NIH-bg-nu-xid; Harlan Laboratories, Indianapolis, Ind.), and the mice were raised for 6 and 12 weeks.

After that, the sample tissues were harvested and fixed in 4% paraformaldehyde, decalcified in 10% EDTA (pH 7.4), embedded in paraffin, stained with hematoxylin-eosin (H-E) (Vector Labs), or conducted Immunohistochemical analysis. To immunohistochemical analysis, proteins were detected with anti-DSP antibody diluted 1:150 as the primary antigen, and goat anti-rabbit IgG (Vector Labs) labeled with biotin as secondary antigen.

Collagen staining was conducted by using a Masson's Trichrome Stain Kit (Cat. 25088-100) of Polysciences, co.

Quantitative analysis of newly formed hard tissue was analyzed using the LS starter program (OLYMPUS Soft Imaging Solution, Muster, Germany). The proportion of newly formed hard tissue was calculated as the percentage of the area of newly formed hard tissue in the total area.

EXAMPLE 1-6

Scanning Electron Microscope Analysis

The sample tissues were fixed in 2.5% Glutaraldehyde/0.1 M Cacodylate buffer for 30 minutes and reacted in a solution containing 1% osmium tetroxide in 0.1 M Cacodylate buffer for 1 hour. Then, the sample tissues were quickly dehydrated and dried using ethanol, and then the sample tissues were coated with gold and observed with a scanning electron microscope (S-4700, HITACHI, Tokyo, Japan).

EXAMPLE 1-7

Statistical Analysis

Statistical analysis was performed using Student's t-test. All statistical analysis is performed by SPSS software ver. 19.0.

EXAMPLE 2

Experimental Results

Example 2-1. The effect of the peptides for the promotion of dentin or dental pulp tissue and the treating of dentin or dental pulp diseases on the expression level of odontoblast differentiation marker Dspp gene The Dspp gene is used as a marker for odontoblast cell differentiation and is known as an essential gene for dentin calcification. Therefore, it was confirmed that the peptide of the present invention has an effect of promoting the expression of the Dspp gene, which is odontoblast differentiation marker gene, and promoting odontoblast and the formation of dentin.

The human dental pulp cells (hDPCs) cultured in Example 3 were treated with the peptides (concentration of 10 μg/ml) of each group synthesized in Example 1-1, and cultured for 48 hours. Then, mRNA levels of an odontoblast differentiation marker Dspp gene expressed in the human dental pulp cells were measured, and a ratio of the measured Dspp mRNA level relative to a Dspp mRNA level measured in a control group was calculated, respectively (Tables 18 to 33).

And, the average value of mRNA levels of the Dspp gene measured according to the peptides of each group of Tables 1 to 3 was compared for each group (FIG. 1A). Specifically, the new peptides of the present invention lacking the substitution or partial sequence of amino acid nucleotide sequences are grouped as shown in Tables 1 to 3, and the new peptides of each group are used for expression of Dspp, a blast cell differentiation marker gene, in human dental pulp cells. As a result, showing the effect, a graph showing the average value of each group measured by quantitative real-time PCR of the level of Dspp mRNA in human dental pulp cells is shown in FIG. 1A. In this case, human dental pulp cells that were not treated with the peptide of the present invention were used as a control.

In addition, the average value of mRNA levels of the Dspp gene measured according to the peptides of each group of Tables 4 to 16 was compared for each group (FIG. 1B). Specifically, the new peptides of the present invention lacking the substitution or partial sequence of amino acid base sequences are grouped as shown in Tables 4 to 16, and the new peptides of each group are expressed in the expression of Dspp, a blast cell differentiation marker gene, in human dental pulp cells. As a result, showing the effect, a graph showing the average value of each group measured by quantitative real-time PCR of the level of Dspp mRNA in human dental pulp cells is shown in FIG. 1B. In this case, human dental pulp cells that were not treated with the peptide of the present invention were used as a control.

The expression level of the Dspp gene was measured through RT-PCR and real-time PCR analysis described in Example 1-4. In this regard, GAPDH gene was used as an internal control. The experiments were performed in triplicate, and then mean values and standard deviations thereof were taken as measured values. The base sequence of the primers is described in Table 17 above.

TABLE 18

Effects of peptides of group 1 on mRNA level of Dspp gene

| | mRNA level of Dspp gene | |
|---|---|---|
| SEQ ID NO: | Mean | Standard deviation |
| 1 | 7.371 | 0.093 |
| 2 | 7.171 | 0.121 |
| 3 | 6.512 | 0.209 |
| 4 | 7.071 | 0.192 |
| 5 | 6.893 | 0.07 |
| 6 | 6.931 | 0.119 |
| 7 | 6.881 | 0.321 |
| 8 | 6.531 | 0.2025 |

TABLE 19

Effects of peptides of group 2 on mRNA level of Dspp gene

| | mRNA level of Dspp gene | |
|---|---|---|
| SEQ ID NO: | Mean | Standard deviation |
| 9 | 7.543 | 0.132 |
| 10 | 6.996 | 0.352 |
| 11 | 7.385 | 0.271 |

TABLE 19-continued

Effects of peptides of group 2 on mRNA level of Dspp gene

| | mRNA level of Dspp gene | |
|---|---|---|
| SEQ ID NO: | Mean | Standard deviation |
| 12 | 7.548 | 0.327 |
| 13 | 6.655 | 0.377 |
| 14 | 6.839 | 0.241 |
| 15 | 6.764 | 0.289 |
| 16 | 7.739 | 0.357 |

TABLE 20

Effects of peptides of group 3 on mRNA level of Dspp gene

| | mRNA level of Dspp gene | |
|---|---|---|
| SEQ ID NO: | Mean | Standard deviation |
| 17 | 7.712 | 0.219 |
| 18 | 7.319 | 0.192 |
| 19 | 7.931 | 0.192 |
| 20 | 7.553 | 0.299 |
| 21 | 7.893 | 0.132 |
| 22 | 7.412 | 0.372 |
| 23 | 9.171 | 0.381 |
| 24 | 8.512 | 0.411 |

TABLE 21

Effects of peptides of group 4 on mRNA level of Dspp gene

| | mRNA level of Dspp gene | |
|---|---|---|
| SEQ ID NO: | Mean | Standard deviation |
| 25 | 2.491 | 0.453 |
| 26 | 2.623 | 0.273 |
| 27 | 2.213 | 0.302 |
| 28 | 2.781 | 0.5 |
| 29 | 2.926 | 0.292 |
| 30 | 2.011 | 0.311 |
| 31 | 2.432 | 0.52 |
| 32 | 2.303 | 0.299 |

TABLE 22

Effects of peptides of group 5 on mRNA level of Dspp gene

| | mRNA level of Dspp gene | |
|---|---|---|
| SEQ ID NO: | Mean | Standard deviation |
| 33 | 3.615 | 0.53 |
| 34 | 3.727 | 0.495 |
| 35 | 3.017 | 0.293 |
| 36 | 3.256 | 0.444 |
| 37 | 3.303 | 0.671 |
| 38 | 2.099 | 0.506 |
| 39 | 3.412 | 0.279 |
| 40 | 3.109 | 0.395 |

TABLE 23

Effects of peptides of group 6 on mRNA level of Dspp gene

| SEQ ID NO: | mRNA level of Dspp gene | |
|---|---|---|
| | Mean | Standard deviation |
| 41 | 2.937 | 0.333 |
| 42 | 2.808 | 0.501 |
| 43 | 2.435 | 0.432 |
| 44 | 2.517 | 0.296 |
| 45 | 3.051 | 0.433 |
| 46 | 2.733 | 0.198 |
| 47 | 2.439 | 0.287 |
| 48 | 2.602 | 0.333 |

TABLE 24

Effects of peptides of group 7 on mRNA level of Dspp gene

| SEQ ID NO: | mRNA level of Dspp gene | |
|---|---|---|
| | Mean | Standard deviation |
| 49 | 1.631 | 0.137 |
| 50 | 1.803 | 0.208 |
| 51 | 1.569 | 0.111 |
| 52 | 1.949 | 0.327 |
| 53 | 1.422 | 0.09 |
| 54 | 1.638 | 0.214 |
| 55 | 2 | 0.396 |
| 56 | 1.909 | 0.55 |

TABLE 25

Effects of peptides of group 8 on mRNA level of Dspp gene

| SEQ ID NO: | mRNA level of Dspp gene | |
|---|---|---|
| | Mean | Standard deviation |
| 57 | 2.415 | 0.375 |
| 58 | 2.677 | 0.601 |
| 59 | 2.463 | 0.222 |
| 60 | 2.089 | 0.163 |
| 61 | 1.909 | 0.307 |
| 62 | 2.752 | 0.482 |
| 63 | 2.373 | 0.394 |
| 64 | 1.829 | 0.201 |

TABLE 26

Effects of peptides of group 9 on mRNA level of Dspp gene

| SEQ ID NO: | mRNA level of Dspp gene | |
|---|---|---|
| | Mean | Standard deviation |
| 65 | 2.201 | 0.461 |
| 66 | 2.072 | 0.366 |
| 67 | 2.452 | 0.509 |
| 68 | 2.343 | 0.419 |
| 69 | 1.899 | 0.382 |
| 70 | 1.947 | 0.247 |
| 71 | 2.052 | 0.233 |
| 72 | 1.739 | 0.188 |

TABLE 27

Effects of peptides of group 10 on mRNA level of Dspp gene

| SEQ ID NO: | mRNA level of Dspp gene | |
|---|---|---|
| | Mean | Standard deviation |
| 73 | 2.208 | 0.366 |
| 74 | 2.105 | 0.273 |
| 75 | 2.624 | 0.522 |
| 76 | 2.394 | 0.432 |
| 77 | 1.939 | 0.337 |
| 78 | 2.109 | 0.159 |
| 79 | 2.403 | 0.601 |
| 80 | 2.636 | 0.573 |

TABLE 28

Effects of peptides of group 11 on mRNA level of Dspp gene

| SEQ ID NO: | mRNA level of Dspp gene | |
|---|---|---|
| | Mean | Standard deviation |
| 81 | 1.757 | 0.372 |
| 82 | 1.909 | 0.269 |
| 83 | 2.001 | 0.227 |
| 84 | 2.101 | 0.373 |
| 85 | 1.838 | 0.401 |
| 86 | 1.736 | 0.317 |
| 87 | 1.888 | 0.444 |
| 88 | 1.539 | 0.132 |

TABLE 29

Effects of peptides of group 12 on mRNA level of Dspp gene

| SEQ ID NO: | mRNA level of Dspp gene | |
|---|---|---|
| | Mean | Standard deviation |
| 89 | 1.635 | 0.214 |
| 90 | 1.797 | 0.323 |
| 91 | 1.913 | 0.333 |
| 92 | 1.498 | 0.111 |
| 93 | 1.892 | 0.274 |
| 94 | 1.487 | 0.099 |
| 95 | 1.939 | 0.295 |
| 96 | 2.011 | 0.199 |

TABLE 30

Effects of peptides of group 13 on mRNA level of Dspp gene

| SEQ ID NO: | mRNA level of Dspp gene | |
|---|---|---|
| | Mean | Standard deviation |
| 97 | 1.515 | 0.107 |
| 98 | 1.479 | 0.106 |
| 99 | 1.737 | 0.207 |
| 100 | 1.599 | 0.166 |
| 101 | 1.674 | 0.109 |
| 102 | 1.855 | 0.299 |
| 103 | 1.737 | 0.107 |
| 104 | 1.878 | 0.201 |

TABLE 31

Effects of peptides of group 14 on mRNA level of Dspp gene

| SEQ ID NO: | mRNA level of Dspp gene | |
|---|---|---|
| | Mean | Standard deviation |
| 105 | 1.664 | 0.085 |
| 106 | 1.673 | 0.207 |
| 107 | 1.935 | 0.372 |
| 108 | 1.495 | 0.091 |
| 109 | 1.756 | 0.201 |
| 110 | 1.595 | 0.099 |
| 111 | 1.918 | 0.175 |
| 112 | 1.699 | 0.143 |

TABLE 32

Effects of peptides of group 15 on mRNA level of Dspp gene

| SEQ ID NO: | mRNA level of Dspp gene | |
|---|---|---|
| | Mean | Standard deviation |
| 113 | 1.778 | 0.205 |
| 114 | 1.849 | 0.337 |
| 115 | 1.707 | 0.199 |
| 116 | 1.693 | 0.075 |
| 117 | 1.929 | 0.193 |
| 118 | 2.015 | 0.151 |
| 119 | 2.121 | 0.337 |
| 120 | 1.878 | 0.116 |

TABLE 33

Effects of peptides of group 16 on mRNA level of Dspp gene

| SEQ ID NO: | mRNA level of Dspp gene | |
|---|---|---|
| | Mean | Standard deviation |
| 121 | 2.024 | 0.298 |
| 122 | 1.979 | 0.303 |
| 123 | 1.837 | 0.111 |
| 124 | 2.017 | 0.402 |
| 125 | 2.082 | 0.377 |
| 126 | 1.798 | 0.163 |
| 127 | 1.888 | 0.099 |
| 128 | 1.765 | 0.375 |

FIG. 1A is a graph showing the results of comparing the expression levels of the dentin sialophosphoprotein (Dspp), odontoblast differentiation marker gene, in human dental pulp cells (hDPCs) treated with the novel peptide of the present invention. Refer to FIG. 1A and Table 18 to Table 20, compared to the mRNA level of the Dspp gene, an odontoblast differentiation marker, measured in human dental pulp cells (control) not treated with the peptide of the present invention, when the peptide of the present invention is treated, it can be seen that all of the mRNA levels of the Dspp gene increased by about 6 to 8 times. Especially when treated with the peptide of group 3, it showed the highest Dspp mRNA expression value. FIG. 1B is another graph showing the result of comparing the expression levels of Dspp, odontoblast differentiation marker gene, in human dental pulp cells (hDPCs) treated with the novel peptide of the present invention. Refer to FIG. 1B and Table 21 to Table 33, compared to the mRNA level of the Dspp gene, a marker of differentiation of odontoblast differentiation measured in human dental pulp cells (control) without treatment of the peptide of the present invention, when the peptide of the present invention is treated, it can be seen that all of the mRNA levels of the Dspp gene increased by about 1.5 to 3 times.

EXAMPLE 2-2

Effects of Peptides for Promoting Regeneration of Dentin or Dental Pulp Tissues and Treating Dental Pulp Diseases on Expression Levels of Odontoblast Differentiation Marker Gene, Nestin The results of Example 2-1 showed that the peptides of the present invention might increase the Dspp mRNA level, for example, all groups of peptides can increase the mRNA level of the Dspp gene by more than 1.5 times, and even more than 3 times, and in particular, the peptides of Group 1 and Group 3 may increase the Dspp mRNA level at least 6 times or higher.

Accordingly, it was examined whether the peptides of Group and Group 3 may increase mRNA levels of other odontoblast differentiation marker genes, Nestin.

Figure 1C:
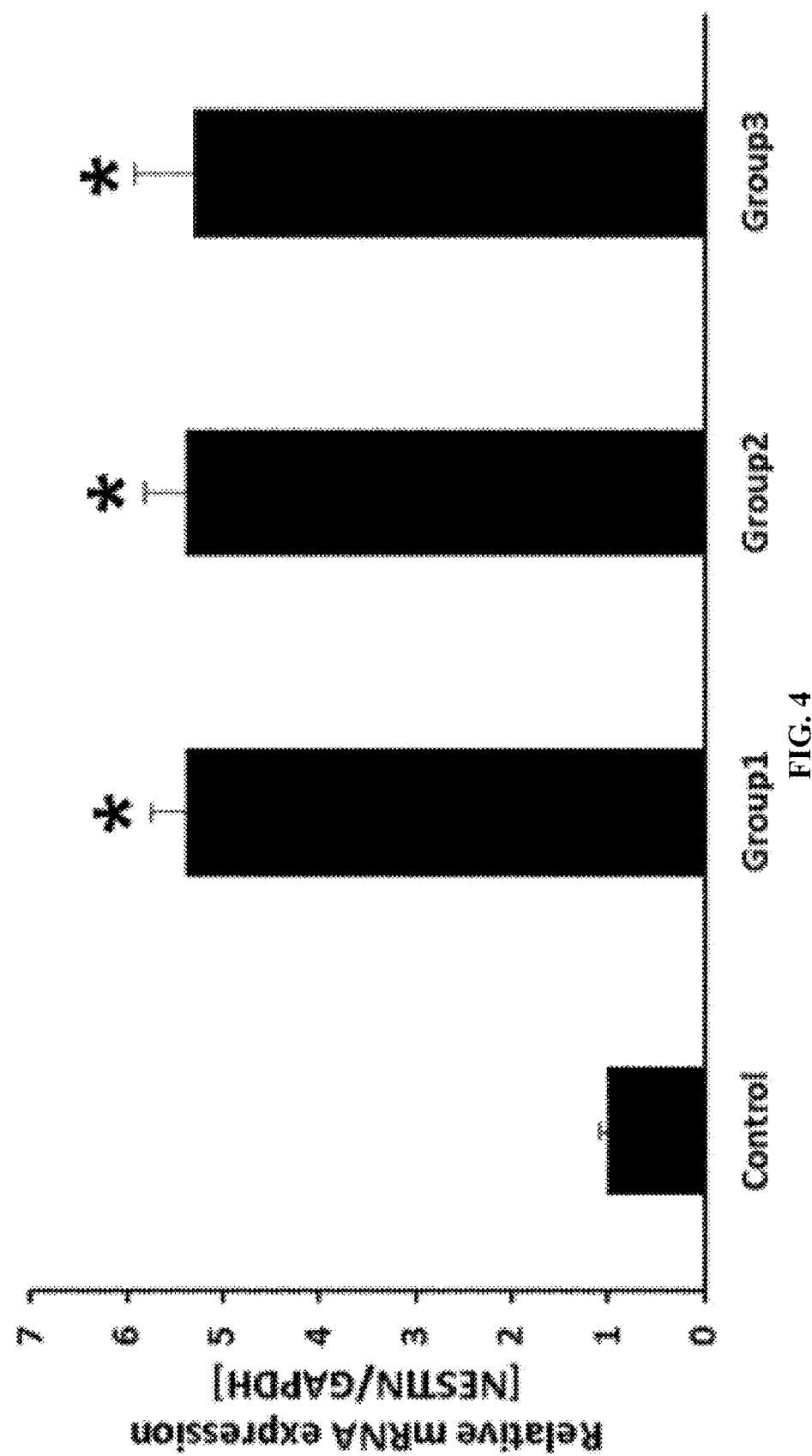
FIG. 1C is a graph showing the results of comparing the expression levels of Nestin, odontoblast differentiation marker genes, in human dental pulp cells (hDPCs) treated with the peptide of the present invention.

Briefly, experiments were performed in the same and similar manner as in Example 2-1, except that the following primers were used. The effects of the peptides of the present invention on expression levels of Nestin genes were measured, and the calculated mean values were compared between the groups (FIG. 1C). In this regard, human dental pulp cells that were treated with none of the peptides of the present invention were used as a control group.

FIG. 1C is a graph showing the results of comparing the expression levels of Nestin, odontoblast differentiation marker genes, in human dental pulp cells (hDPCs) treated with the peptide of the present invention. As shown in FIG. 1C, the group treated with the peptide of the present invention (Group 1, 2, 3) compared to the control group, it can be seen that the expression level of the Nestin gene, which is a marker of differentiation of the odontoblast differentiation, is increased by 5 times or more.

The above Dspp and Nestin genes are known as genes involved in odontoblast differentiation and dentin mineralization, which infers that the peptides of the present invention may exhibit the effect of promoting dentin regeneration.

EXAMPLE 2-3

Effect of Osteoblasts and/or Cementoblasts Promotion and Periodontal Disease Treatment Peptide on the Expression Levels of BSP Gene, Osteoblasts and Cementoblasts Differentiation Marker Gene The BSP gene is used as a marker for differentiating osteoblasts and cementoblasts, and is known as an essential gene for calcification of bone and cementum. Therefore, in order to confirm the effect of the novel peptide of the present invention on the expression of the BSP gene, bone stem cell and a cementum cell differentiation marker gene, human-derived mesenchymal stem cells cultured by performing the method of Example 1-2 above (after treating each group of peptides in human bone marrow mesenchymal stem cells (hBMSCs)), BSP gene expression was confirmed by real-time PCR.

Briefly, except for using a different primer, the same and similar methods as in Example 2-1 were performed to measure the effect of the peptide of the present invention on the expression level of the BSP gene, and was measured for each group. The average level was compared (FIG. 2A, FIG.

2B). Specifically, in the novel peptides of the present invention grouped as shown in Tables 1 to 3, each group of new peptides expresses bone and cementum differentiation marker gene BSP (Bone sialoprotein) in human-derived mesenchymal stem cells (hBMSCs). As a result, showing the effect, the result of measuring the level of BSP mRNA in human-derived mesenchymal stem cells by quantitative real-time PCR is shown in FIG. 2A. In addition, in the novel peptides of the present invention grouped as shown in Tables 4 to 16, as a result showing the effect of each group of new peptides on the expression of BSP, a bone and cementum differentiation marker gene, in human-derived mesenchymal stem cells, the result of measuring the level of BSP mRNA in the derived mesenchymal stem cells by quantitative real-time PCR is shown in FIG. 2B.

At this time, the peptide was treated at a concentration of 10 μg/ml. And as a control, human bone marrow mesenchymal stem cells not treated with the peptide of the present invention were used.

FIG. 2A is a graph showing the results of comparing the expression level of the BSP gene, a bone and cementum differentiation marker gene, in human-derived mesenchymal stem cells (hBMSCs) treated with the peptide of the present invention. As shown in FIG. 2A, the group treated with the peptide of the present invention (Group 1, 2, 3), it can be seen that the BSP gene expression increased by about 9 to 13 times or more compared to the control. In particular, when treated with the peptide of group 3, it showed the highest BSP mRNA expression value.

FIG. 2B is a graph showing the results of comparing the expression level of the BSP gene, a bone and cementum differentiation marker gene, in human-derived mesenchymal stem cells (hBMSCs) treated with the peptide of the present invention. As shown in FIG. 2B, the group treated with the peptide of the present invention (Group 4 to Group 16), can be found that the BSP gene expression is increased by about 3 to 9 times or more, and 12 times or more, compared to the control. In particular, when treated with the peptide of group 11, it showed the highest BSP mRNA expression value.

As the BSP gene is used as a marker for differentiating osteoblasts and cementoblasts and is known as a gene involved in the process of calcification of bone and cementum, it was analyzed that the peptide provided in the present invention would have an effect of promoting regeneration of bone and cementum.

EXAMPLE 2-4

Hard Tissue Formation of Human Dental Pulp Cells (hDPCs) by Novel Peptides In Vivo for 6 Weeks (1) Histomorphological Analysis FIG. 1A, FIG. 1B, FIG. 1C, FIG. 2A, and FIG. 2B, based on the results of the in vitro experiments, in order to measure the effect of the peptide of the present invention on hard tissue formation in vivo, described in Examples 1-5 above As described, human dental pulp cells (hDPCs) and 100 mg of hydroxyapatite/tricalcium phosphate (HA/TCP) were mixed with 0.5 μg fibrin gel, respectively, with 10 μg of group 3 peptides (eg, SEQ ID NO: 24) to prepare an implant. The implant was transplanted into the subcutaneous tissue of a mouse with a compromised immune system. At this time, as a control, a transplanted implant containing no peptide of the present invention was used. After 6 weeks of transplantation, as described in Example 1-5 above, a sample was taken and then the newly formed hard tissue was quantitatively analyzed using the LS starter program, and the results are shown in FIG. 3.

FIG. 3 shows the results of measuring the amount of newly formed hard tissue using human dental pulp cells (hDPCs) for 6 weeks in vivo. As shown in FIG. 3, the ratio of hard tissue formation after 6 weeks of transplantation was increased by about 2 times or more in the group treated with the novel peptide (Group 3, 29.6%) compared to the control (Control, 13.5%).

Figure 4:
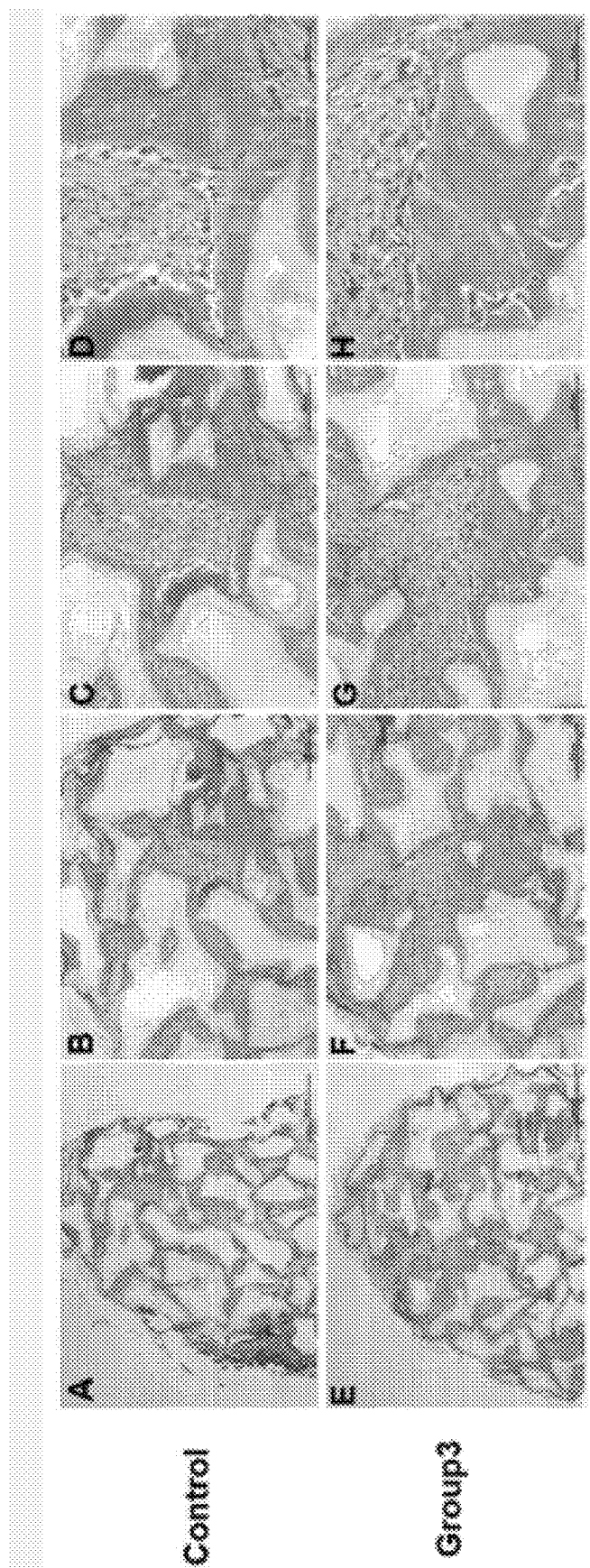
FIG. 4 shows microscopic images showing the histomorphological analysis of the hard tissue formed using human dental pulp cells (hDPCs) for 6 weeks in vivo, in which A to D show the results of transplantation of a control implant prepared by mixing hDPCs and 100 mg HA/TCP in a 0.5% fibrin gel for 6 weeks in a mouse with a compromised immune system, and in which E to H show the results of transplantation of implant prepared by mixing hDPCs and 100 mg HA/TCP, 10 μg peptide (group 3) in a 0.5% fibrin gel for 6 weeks in a mouse with a compromised immune system, respectively (scale bar: A, E 500 μm, B, F 200 μm, C, G 100 μm, D, H 50 μm).

FIG. 4 is a microscopic image showing the histomorphological analysis of the hard tissue formed using human dental pulp cells (hDPCs) for 6 weeks in vivo, A to D show the results of transplantation of a control implant prepared by mixing hDPCs and 100 mg HA/TCP in a 0.5% fibrin gel for 6 weeks in a mouse with compromised immune systems and E to H show the results of transplantation of hDPCs and 100 mg HA/TCP with 0.5% fibrin gel, respectively, together with 10 μg of group 3 peptide, in a mouse with compromised immune systems for 6 weeks (scale bar: A, E 500 μm; B, F 200 μm; C, G 100 μm; D, H 50 μm).

As shown in FIG. 4, as a result of histomorphological analysis through hematoxylin-eosin staining, in the control group (FIG. 4A to FIG. 4D) not containing the peptide of the present invention and a group containing the peptide of the present invention (FIG. 4E to FIG. 4H) were observed that bone-like tissue and dentin-pulp-like tissue were formed in the substrate of the calcified tissue around the HA/TCP particles.

(2) Collagen Staining Analysis

Collagen is the most abundant organic matrix in dentin, bone and cementum, and serves to accommodate deposited minerals. Accordingly, collagen staining was performed to confirm the accumulation of collagen protein in the calcified tissue formed in each experimental group of the histomorphological analysis.

Figure 5:
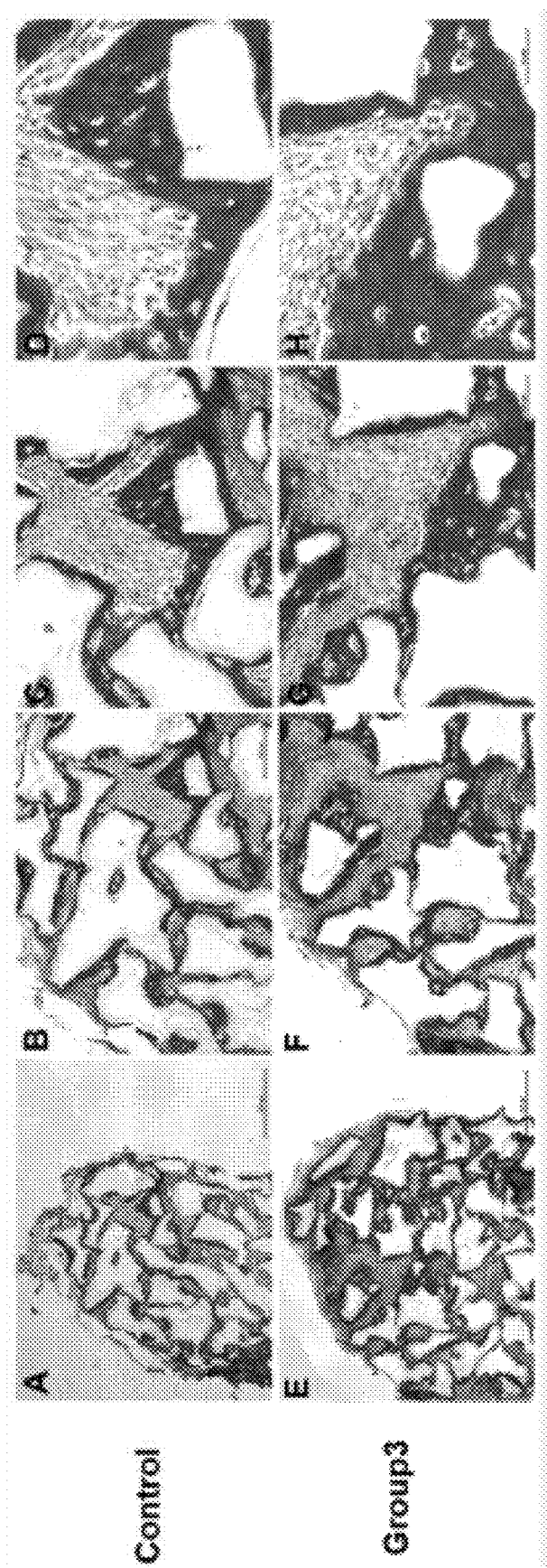
FIG. 5 shows microscopic images showing the level of collagen formation in hard tissue formed using human dental pulp cells (hDPCs) for 6 weeks in vivo, in which A to D show the results of transplantation of a control implant prepared by mixing hDPCs and 100 mg HA/TCP in a 0.5% fibrin gel for 6 weeks in a mouse with a compromised immune system, and in which E to H show the results of transplantation of implant prepared by mixing hDPCs, 100 mg HA/TCP, and 10 μg peptide (group 3) in a 0.5% fibrin gel for 6 weeks in a mouse with a compromised immune system, respectively (scale bar: A, E 500 μm, B, F 200 μm, C, G 100 μm, D, H 50 μm).

FIG. 5 shows microscopic images showing the level of collagen formation in hard tissue formed using human dental pulp cells (hDPCs) for 6 weeks in vivo, A to D show the results of transplantation of a control implant prepared by mixing hDPCs and 100 mg HA/TCP in a 0.5% fibrin gel for 6 weeks in a mouse with compromised immune systems and E to H show the results of transplantation of hDPCs and 100 mg HA/TCP with 0.5% fibrin gel, respectively, together with 10 μg of group 3 peptide, in a mouse with compromised immune systems for 6 weeks (scale bar: A, E 500 μm; B, F 200 μm; C, G 100 μm; D, H 50 μm). The formed hard tissue was stained by the method of collagen stain (Masson's trichrome stain).

As shown in FIG. 5, compared to the control group (FIG. 5A to 5D), in the group containing the peptide of the present invention (FIG. 5E to 5H), it was confirmed that the formation level of collagen was increased.

(3) Immunohistochemical Analysis

The expression of DSP, odontoblast specific differentiation marker gene, was confirmed by immunohistochemical analysis.

Figure 6:
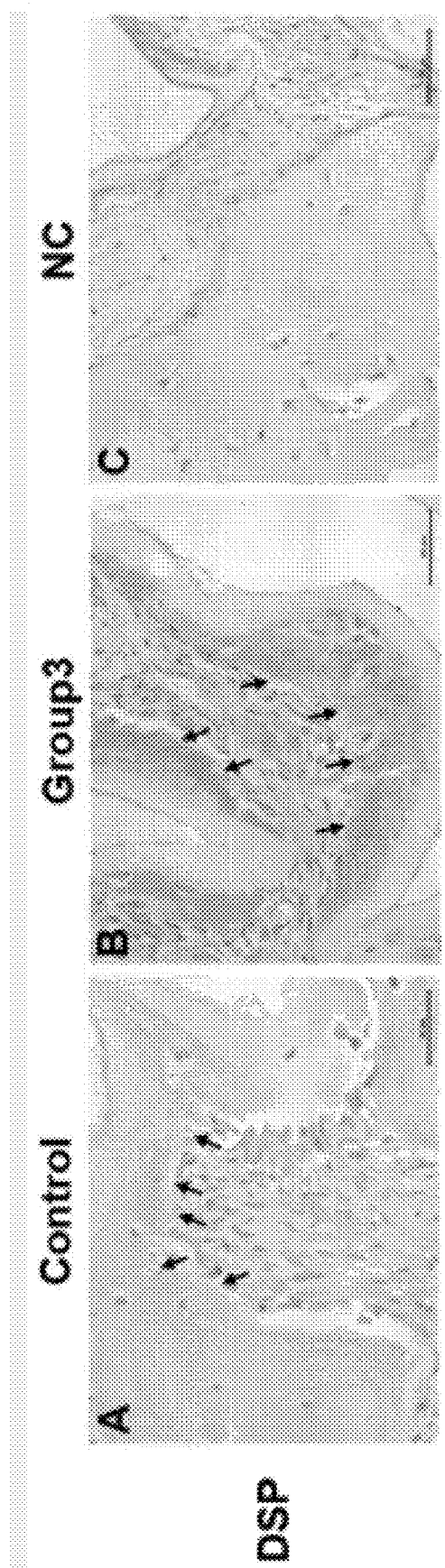
FIG. 6. shows immunostaining images showing the analysis of the expression level of DSP, odontoblast differentiation marker gene, using immunostaining method, in hard tissue formed using human dental pulp cells (hDPCs) for 6 weeks in vivo, in which A shows the results of transplanting the implant prepared by mixing hDPCs and 100 mg HA/TCP in a 0.5% fibrin gel in a mouse with a compromised immune system for 6 weeks, in which B shows the results of transplanting the implant prepared by mixing hDPCs 100 mg HA/TCP, and 10 μg peptide (group 3) in a 0.5% fibrin gel in a mouse with a compromised immune system for 6 weeks. A and B are immunostained of the formed hard tissue using anti-DSP antibody. C is a negative control of immunohistochemical analysis treated only with secondary antibodies. Arrows in A and B indicate the expression of DSP in newly formed calcified tissue. The scale bar is 50 μm.

FIG. 6 is an immunostaining picture showing the analysis of the expression level of DSP, a marker for differentiation of blast cells using immunostaining method, in hard tissue formed using human dental pulp cells (hDPCs) for 6 weeks in vivo, A to D show the results of transplantation of a control implant prepared by mixing hDPCs and 100 mg HA/TCP in a 0.5% fibrin gel for 6 weeks in a mouse with compromised immune systems and E to H show the results of transplantation of hDPCs and 100 mg HA/TCP with 0.5% fibrin gel, respectively, together with 10 μg of group 3 peptide, in a mouse with compromised immune systems for 6 weeks. A and B were immunostained using the anti-DSP antibody. C is a negative control of immunohistochemical analysis treated with only secondary antibodies. Arrows marked A and B indicate the expression of DSP in newly formed calcified tissue. The scale bar is 50 μm.

As shown in FIG. 6, the control group (FIG. 6A) was weakly expressed in DSP in newly formed dentin-pulp-like tissue, but the calcified tissue in which DSP was newly formed in the group containing the peptide of the present invention (FIG. 6B) was strongly expressed. FIG. 6C shows that in the immunohistochemical analysis, the secondary antibody-treated negative control group was not stained with DSP.

EXAMPLE 2-5

Hard Tissue Formation of Human Dental Pulp Cells (hDPCs) by Novel Peptides In Vivo for 12 Weeks Except for raising the implanted mouse for 12 weeks, the method of Example 2-4 was performed to analyze hard tissue formation in human dental pulp cells.

Figure 7:
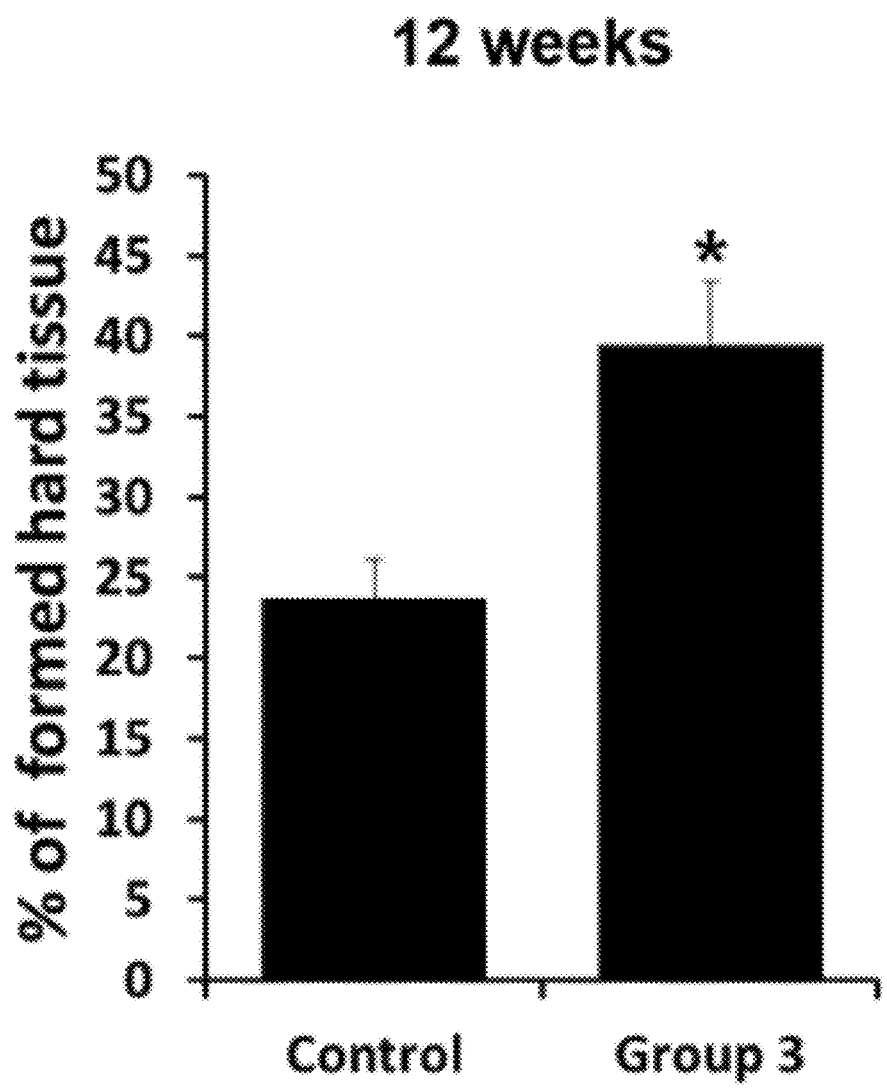
FIG. 7. shows the result of measuring the amount of newly formed hard tissue using human dental pulp cells (hDPCs) for 12 weeks in vivo.

FIG. 7 shows the results of measuring the amount of newly formed hard tissue using human dental pulp cells (hDPCs) for 12 weeks in vivo. As shown in FIG. 7, the ratio of hard tissue formation after 12 weeks of transplantation was increased by about 2 times or more in the group treated with the novel peptide (Group 3, 39.5%) compared to the control (Control, 23.7%).

Figure 8:
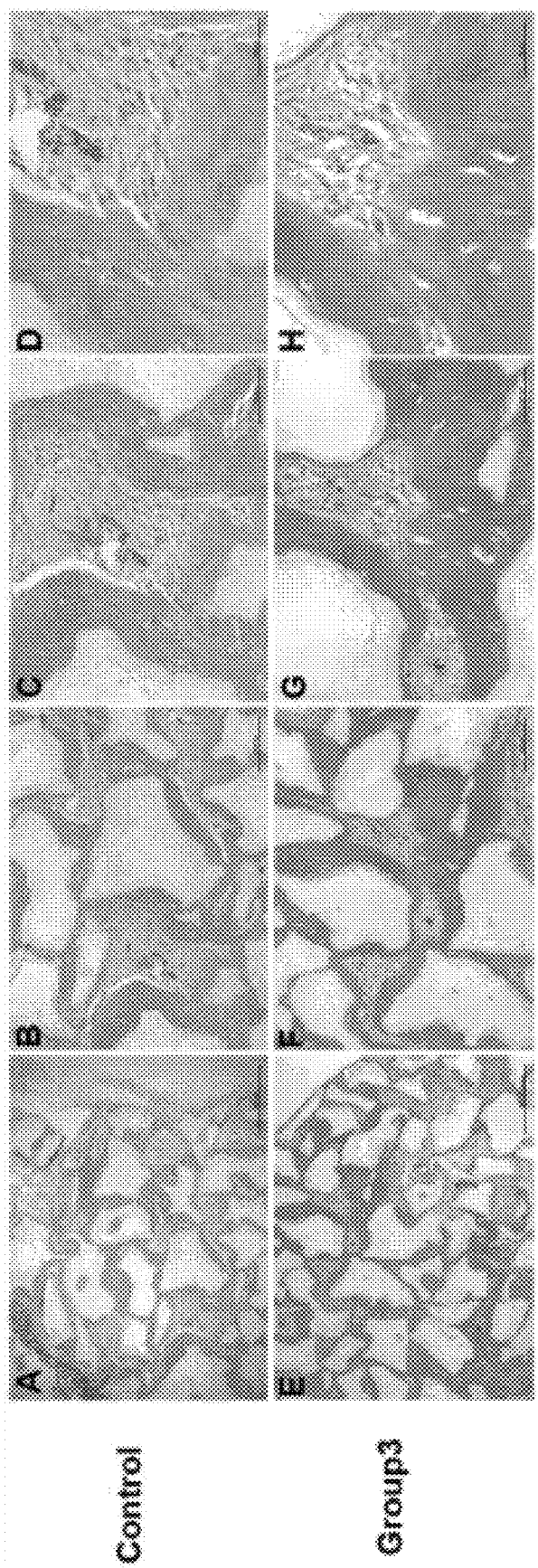
FIG. 8 shows microscopic images showing the histomorphological analysis of the hard tissue formed using human dental pulp cells (hDPCs) for 12 weeks in vivo, in which A to D show the results of transplantation of a control implant prepared by mixing hDPCs and 100 mg HA/TCP in a 0.5% fibrin gel for 12 weeks in a mouse with a compromised immune system, and in which E to H show the results of transplantation of implant prepared by mixing hDPCs and 100 mg HA/TCP, 10 μg peptide (group 3) in a 0.5% fibrin gel for 12 weeks in a mouse with a compromised immune system, respectively (scale bar: A, E 500 μm, B, F 200 μm, C, G 100 μm, D, H 50 μm).

FIG. 8 is a microscopic image showing the histomorphological analysis of the hard tissue formed using human dental pulp cells (hDPCs) for 12 weeks in vivo, A to D show the results of transplantation of a control implant prepared by mixing hDPCs and 100 mg HA/TCP in a 0.5% fibrin gel for 12 weeks in a mouse with compromised immune systems and E to H show the results of transplantation of hDPCs and 100 mg HA/TCP with 0.5% fibrin gel, respectively, together with 10 μg of group 3 peptide, in a mouse with compromised immune systems for 12 weeks (scale bar: A, E 500 μm; B, F 200 μm; C, G 100 μm; D, H 50 μm).

As shown in FIG. 8, as a result of histomorphological analysis through hematoxylin-eosin staining, similar to the case of FIG. 4 (6 weeks transplant) in the control group (FIG. 8A to FIG. 8D) not containing the peptide of the present invention and a group containing the peptide of the present invention (FIG. 8E to FIG. 8H) were observed that bone-like tissue and dentin-pulp-like tissue were formed in the substrate of the calcified tissue around the HA/TCP particles.

(2) Collagen Staining Analysis

Collagen staining was performed to confirm the accumulation of collagen protein in the calcified tissue formed in each experimental group of the histomorphological analysis of Example 2-5.

Figure 9:
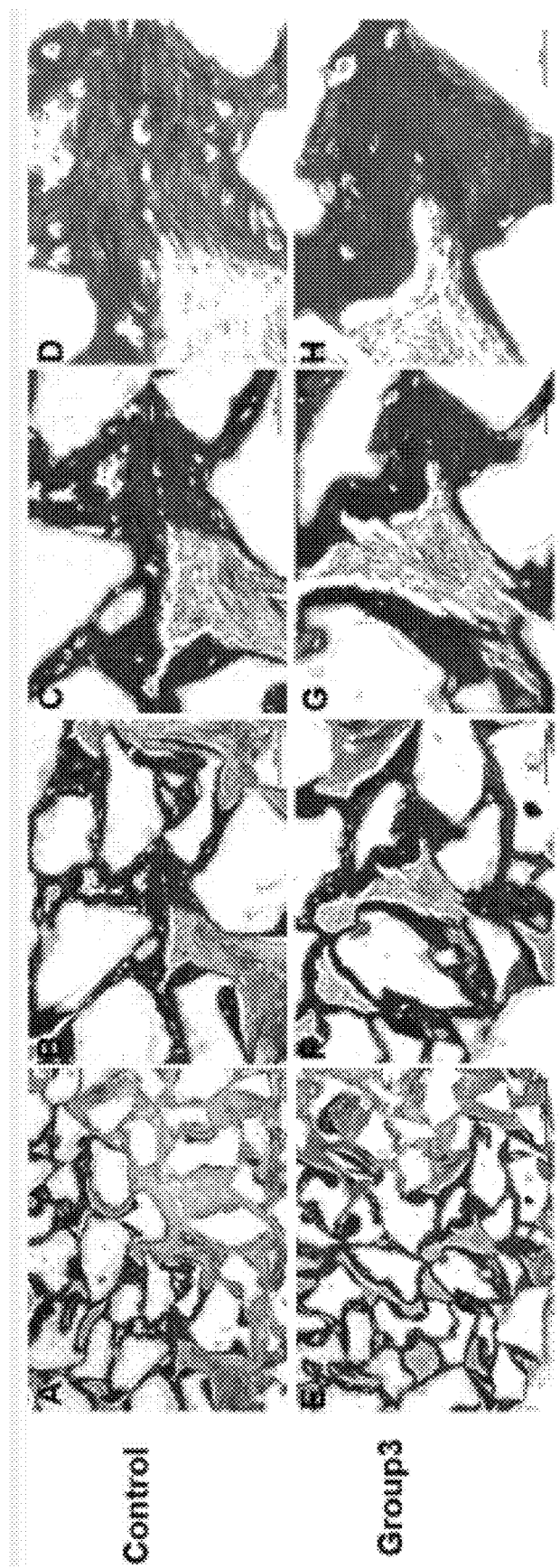
FIG. 9 shows microscopic images showing the level of collagen formation in hard tissue formed using human dental pulp cells (hDPCs) for 12 weeks in vivo, in which A to D show the results of transplantation of a control implant prepared by mixing hDPCs and 100 mg HA/TCP in a 0.5% fibrin gel for 12 weeks in a mouse with a compromised immune system, and in which E to H show the results of transplantation of implant prepared by mixing hDPCs, 100 mg HA/TCP, and 10 μg peptide (group 3) in a 0.5% fibrin gel for 12 weeks in a mouse with a compromised immune system, respectively (scale bar: A, E 500 μm, B, F 200 μm, C, G 100 μm, D, H 50 μm).

FIG. 9 shows microscopic images showing the level of collagen formation in hard tissue formed using human dental pulp cells (hDPCs) for 12 weeks in vivo, A to D show the results of transplantation of a control implant prepared by mixing hDPCs and 100 mg HA/TCP in a 0.5% fibrin gel for 12 weeks in a mouse with compromised immune systems and E to H show the results of transplantation of hDPCs and 100 mg HA/TCP with 0.5% fibrin gel, respectively, together with 10 μg of group 3 peptide, in a mouse with compromised immune systems for 12 weeks (scale bar: A, E 500 μm; B, F 200 μm; C, G 100 μm; D, H 50 μm). The formed hard tissue was stained by the method of collagen stain (Masson's trichrome stain).

As shown in FIG. 9, compared to the control group (FIG. 9A to 9D), in the group containing the peptide of the present invention (FIG. 9E to 9H), it was confirmed that the formation level of collagen was increased.

(3) Immunohistochemical Analysis

The expression of DSP, odontoblast specific differentiation marker gene, was confirmed by immunohistochemical analysis.

Figure 10:
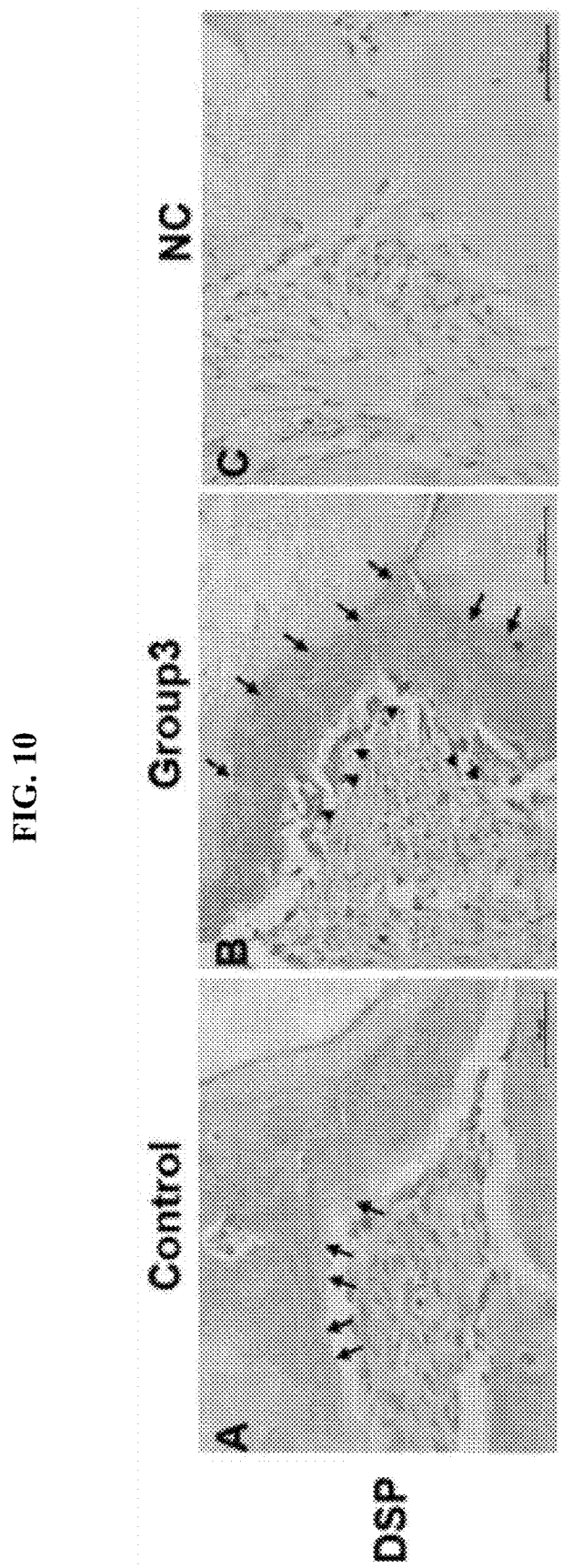
FIG. 10. shows immunostaining images showing the analysis of the expression level of DSP, odontoblast differentiation marker gene, using immunostaining method, in hard tissue formed using human dental pulp cells (hDPCs) for 12 weeks in vivo, in which A shows the results of transplanting the implant prepared by mixing hDPCs and 100 mg HA/TCP in a 0.5% fibrin gel in a mouse with a compromised immune system for 12 weeks, in which B shows the results of transplanting the implant prepared by mixing hDPCs 100 mg HA/TCP, and 10 μg peptide (group 3) in a 0.5% fibrin gel in a mouse with a compromised immune system for 12 weeks. A and B are immunostained of the formed hard tissue using anti-DSP antibody. C is a negative control of immunohistochemical analysis treated only with secondary antibodies. Arrows in A and B indicate the expression of DSP in newly formed calcified tissue. The scale bar is 50 μm.

FIG. 10 is an immunostaining picture showing the analysis of the expression level of DSP, a marker for differentiation of blast cells using immunostaining method, in hard tissue formed using human dental pulp cells (hDPCs) for 12 weeks in vivo, A to D show the results of transplantation of a control implant prepared by mixing hDPCs and 100 mg HA/TCP in a 0.5% fibrin gel for 12 weeks in a mouse with compromised immune systems and E to H show the results of transplantation of hDPCs and 100 mg HA/TCP with 0.5% fibrin gel, respectively, together with 10 μg of group 3 peptide, in a mouse with compromised immune systems for 6 weeks. A and B were immunostained using the anti-DSP antibody. C is a negative control of immunohistochemical analysis treated with only secondary antibodies. Arrows marked A and B indicate the expression of DSP in newly formed calcified tissue. The scale bar is 50 μm.

As shown in FIG. 10, the control group (FIG. 10A) was weakly expressed in DSP in newly formed dentin-pulp-like tissue, but the calcified tissue in which DSP was newly formed in the group containing the peptide of the present invention (FIG. 10B) was strongly expressed. FIG. 10C shows that in the immunohistochemical analysis, the secondary antibody-treated negative control group was not stained with DSP.

Summarizing the results of Examples 2-4 and 2-5, it was found that the novel peptide of the present invention exhibits an effect capable of promoting regeneration of dentin/pulp tissue complexes and bone/cementum-like tissues.

EXAMPLE 2-6

Cell Analysis Using Scanning Electron Microscope of Transplanted Tissue

Scanning electron microscope analysis of the method of Example 1-6 was performed to confirm the differentiation of human dental pulp cells (hDPCs) into odontoblast or osteoblast/cementoblast in the control group and the experimental group treated with the novel peptide for 12 weeks after transplantation was performed.

After 12 weeks, scanning electron microscope analysis was performed by the method of Example 1-6 in order to confirm the differentiation of human dental pulp cells (hDPCs) into odontoblast or osteoblast/cementoblast between the experimental group treated with the novel peptide and the control group.

Figure 11:
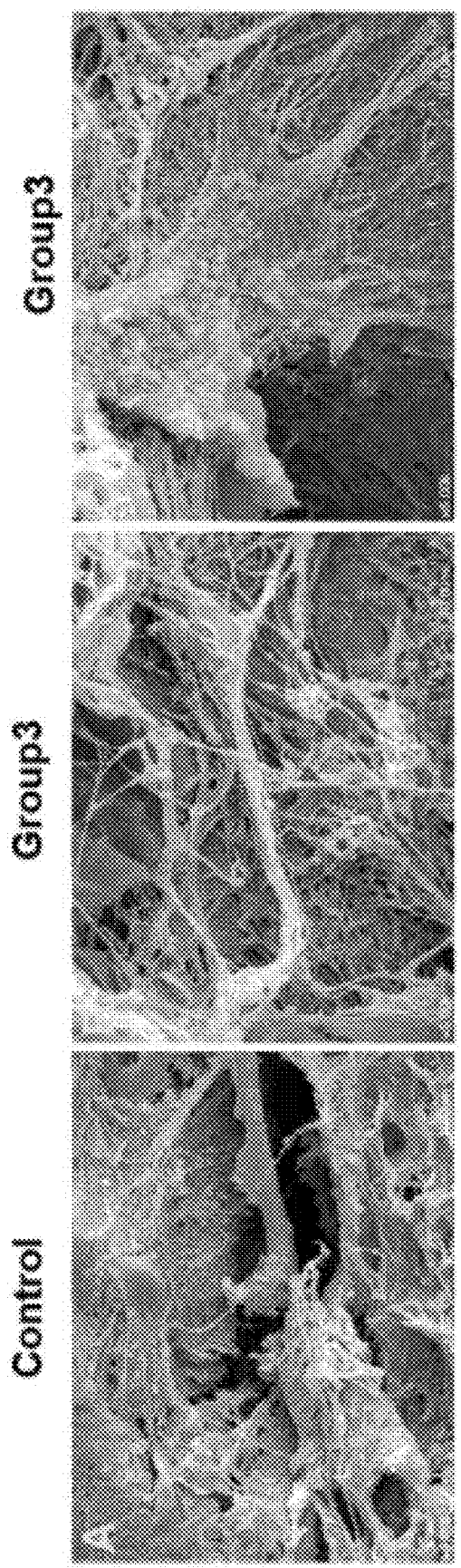
FIG. 11. shows scanning electron microscope (SEM) images showing the analysis of hard tissue formed using human dental pulp cells (hDPCs) for 12 weeks in vivo, in which A shows the results of transplanting the implant prepared by mixing hDPCs and 100 mg HA/TCP in a 0.5% fibrin gel in a mouse with a compromised immune system for 12 weeks, in which B and C show the results of transplanting the implant prepared by mixing hDPCs, 100 mg HA/TCP, and 10 μg peptide (group 3) in a 0.5% fibrin gel in a mouse with a compromised immune system for 12 weeks.

FIG. 11 is an image showing analysis of hard tissue formed using human dental pulp cells (hDPCs) for 12 weeks in vivo using a scanning electron microscope (SEM), wherein A is hDPCs and 100 mg HA/TCP was prepared by mixing 0.5% fibrin gel with control implant, B and C were hDPCs and 100 mg HA/TCP with 10 μg of group 3 peptides, respectively, mixed with 0.5% fibrin gel. It shows the result of the implantation of the implant in a mouse with a compromised immune system for 12 weeks. The scale bar is 10 μm. The formed hard tissue was observed by cells using a scanning electron microscope.

In the control group treated with hDPCs-alone, some of the odontoblast-like cells with incomplete odontoblastic processes were formed around the formed hard tissue (FIG. 11A). In the group treated with the peptide of the present invention (for example, the peptide of group 3), odontoblast-like cells were observed along the formed hard tissue and the odontoblastic processes were also extended toward the formed hard tissue (FIG. 11B). In addition, in the group treated with the peptide of the present invention, it was confirmed that it exhibits the characteristics of typical osteoblasts/cementoblasts with cubic shape attached to the surface of the formed hard tissue (FIG. 11C).

Therefore, it was found that the peptide of the present invention can more effectively form odontoblast and osteoblast/cementoblast.

EXAMPLE 2-7

Obturation Test of Dentinal Tubules In Vivo

In the premolar of a 12-month-old adult dog, a dental bur was used to remove the enamel of the cervical region and expose the dentin. The premolar of exposed dentin was sufficiently washed to completely remove the enamel-dentin fragments generated during vortex formation, followed by removal of moisture.

1.5 μg of the peptide (SEQ ID NO: 24) (group 3) according to the present invention was applied to the inlet of the dentinal tubule on the exposed dentin site, and after 3 weeks, the adult dog was euthanized to extract teeth. Then, a specimen of the extracted tooth was prepared using a diamond saw.

Figure 12:
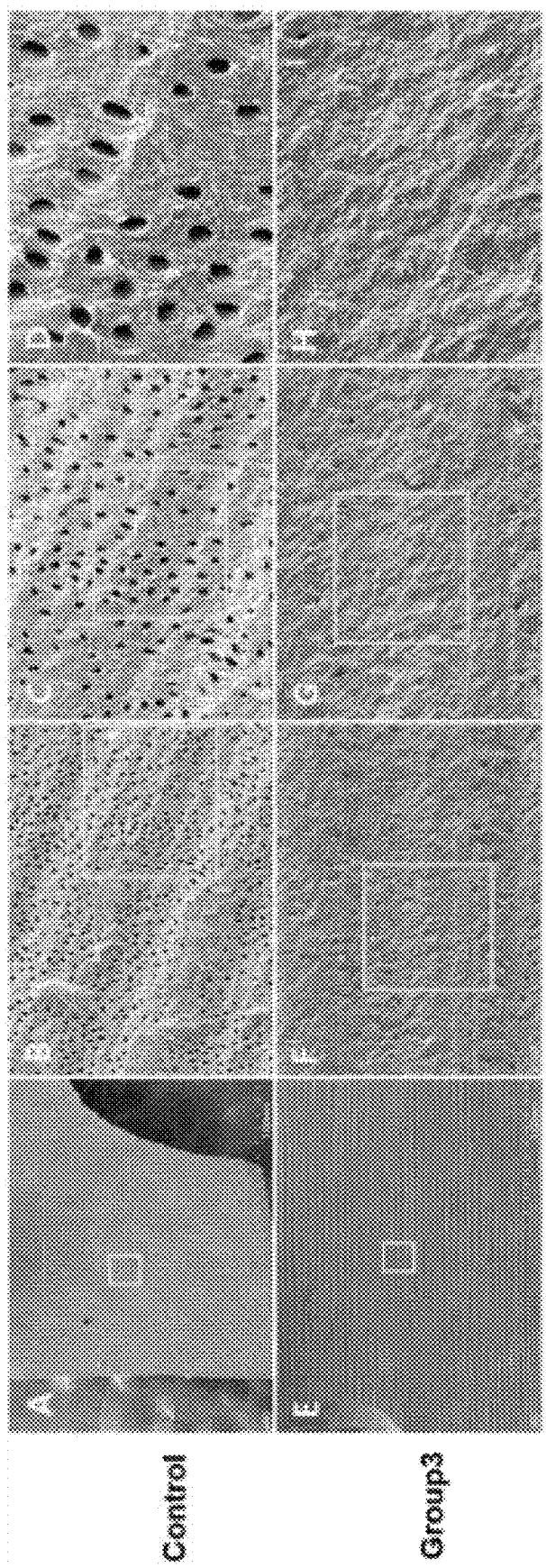
FIG. 12. shows SEM images that the dentinal tubules of the damaged dentin are regenerated and closed with physiological dentin. Individually, B, C, and D of FIG. 12 are enlarged images of A of FIG. 12, respectively. And, F, G, and H of FIG. 12 are enlarged images of E of FIG. 12, respectively. (Scale bar A: 1 mm, B: 50 μm, C: 20 μm, D: 10 μm, E: 1 mm, F: 50 μm, G: 20 μm, H: 10 μm)

And in order to confirm the effect of the novel peptide according to the present invention on the exposed dentinal tubule obturation of the damaged dentin, the ability to close the dentinal tubule was evaluated through a scanning electron microscope and the results are shown in FIG. 12.

Specifically, as shown in FIG. 12A and FIG. 12E, after cutting the lower portion of the dentin injury site, the lower surface (box portion) of the cut surface was observed. As a result of the scanning electron microscope, it was confirmed that the control group without any treatment exposed the dentinal tubules of the lower part of the damaged dentin (FIG. 12A to FIG. 12D). On the other hand, in the experimental group treated with peptides, it can be seen that the exposed dentinal tubules were closed by physiological remineralization (FIG. 12E to FIG. 12H).

EXAMPLE 2-8

Observation of the Damaged Site of Dentin Surface In Vivo

A specimen of teeth extracted from adult dogs was prepared by the same method as in Example 2-7.

Figure 13:
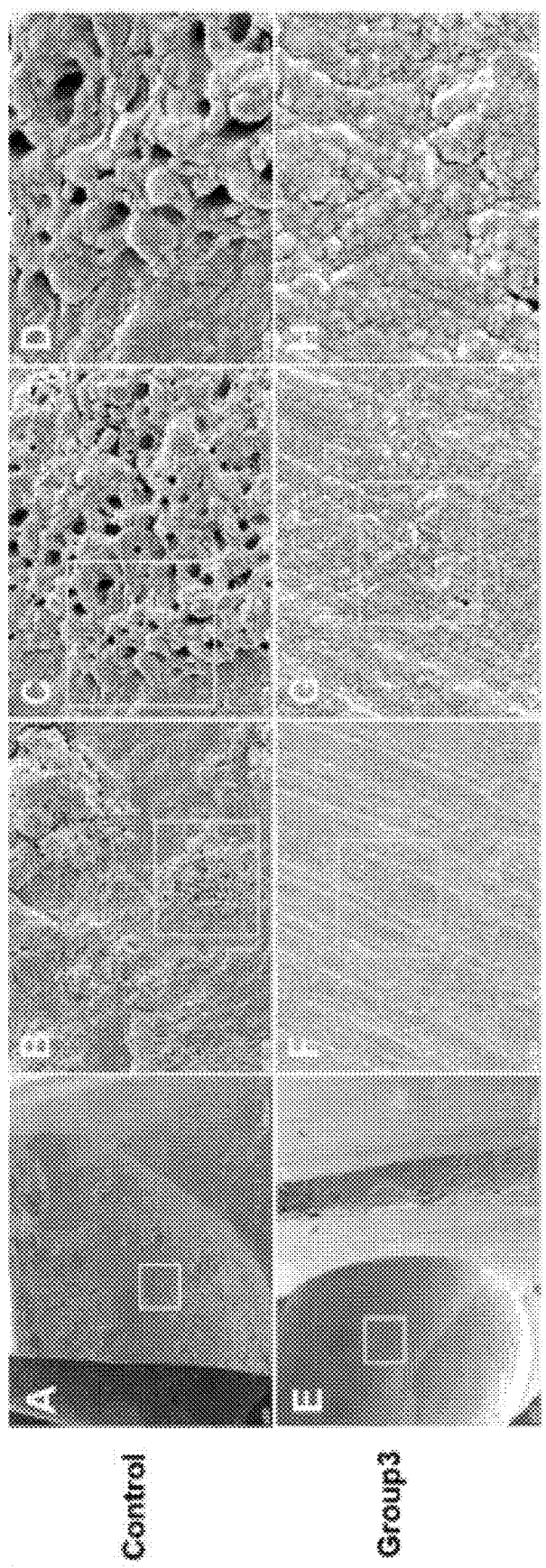
FIG. 13. shows SEM images that the dentinal tubules exposed to the surface of the damaged dentin is closed by physiological remineralization. Individually, B, C, and D of FIG. 13 are enlarged images of A of FIG. 13, respectively. And, F, G, and H of FIG. 13 are enlarged images of E of FIG. 13, respectively. (Scale bar A: 1 mm, B: 50μm, C: 20μm, D: 10μm, E: 1 mm, F: 50μm, G: 20 μm, H: 10 μm)

And to confirm the effect of the novel peptide according to the present invention on the dentinal tubule obturation on the surface of the damaged dentin, the ability to close the dentin tubules on the surface area was evaluated through a scanning electron microscope, and the results are shown in FIG. 13.

As a result of observation by scanning electron microscope, it can be confirmed that the dentinal tubules are exposed on the damaged dentin surface of the control group without any treatment (FIG. 13A to FIG. 13D). On the other hand, in the experimental group treated with the peptide, it can be seen that most of the exposed dentinal tubules were closed (FIG. 13E to FIG. 13H).

This study was supported by the Korea Evaluation Institute of Industrial Technology (KEIT) and funded by the Ministry of Trade, Industry & Energy in 2017 (10078369, "Development of desensitizer using functional peptide inducing dentin regeneration").

While one or more embodiments of the present invention have been described with reference to the figures, it will be understood by those of ordinary skill in the art that various changes in form and details may be made therein without departing from the spirit and scope of the present invention.

The invention claimed is:

1. A method for promoting regeneration of hard tissue in a subject in need thereof, comprising administering an effective amount of a peptide consisting of the amino acid sequence of any one of SEQ ID NOs: 1 to 128 or a composition comprising the peptide to the subject.

2. The method of claim 1, wherein the peptide consists of the amino acid sequence of any one of SEQ ID NOs: 1 to 24.

3. The method of claim 1, wherein the peptide consists of the amino acid sequence of any one of SEQ ID NOs: 25 to 48.

4. The method of claim 1, wherein the peptide consists of the amino acid sequence of any one of SEQ ID NOs: 49 to 128.

5. The method of claim 1, wherein the peptide has a modification selected from the group consisting of an N- or C-terminal acetylation, amidation, or methylation.

6. A method for treating dental-dentin pulp disease or periodontal disease in a subject in need thereof, comprising administering an effective amount of a peptide consisting of the amino acid sequence of any one of SEQ ID NOs: 1 to 128 or a composition comprising the peptide to the subject.

7. The method of claim 6, wherein the peptide consists of the amino acid sequence of any one of SEQ ID NOs: 1 to 24.

8. The method of claim 6, wherein the peptide consists of the amino acid sequence of any one of SEQ ID NOs: 25 to 48.

9. The method of claim 6, wherein the peptide consists of the amino acid sequence of any one of SEQ ID NOs: 49 to 128.

10. The method of claim 6, wherein the peptide has a modification selected from the group consisting of an N- or C-terminal acetylation, amidation, or methylation.

* * * * *

SEQUENCE LISTING

<160> NUMBER OF SEQ ID NOS: 136

<210> SEQ ID NO 1
<211> LENGTH: 7
<212> TYPE: PRT
<213> ORGANISM: Artificial Sequence
<220> FEATURE:
<223> OTHER INFORMATION: Novel peptide

<400> SEQUENCE: 1

Lys Tyr Gln Arg Arg Lys Lys
1               5

<210> SEQ ID NO 2
<211> LENGTH: 7
<212> TYPE: PRT
<213> ORGANISM: Artificial Sequence
<220> FEATURE:
<223> OTHER INFORMATION: Novel peptide

<400> SEQUENCE: 2

Lys Tyr Gln Arg Arg Lys Arg
1               5

```
<210> SEQ ID NO 3
<211> LENGTH: 7
<212> TYPE: PRT
<213> ORGANISM: Artificial Sequence
<220> FEATURE:
<223> OTHER INFORMATION: Novel peptide

<400> SEQUENCE: 3

Lys Tyr Gln Arg Arg Arg Lys
1               5

<210> SEQ ID NO 4
<211> LENGTH: 7
<212> TYPE: PRT
<213> ORGANISM: Artificial Sequence
<220> FEATURE:
<223> OTHER INFORMATION: Novel peptide

<400> SEQUENCE: 4

Lys Tyr Gln Arg Arg Arg Arg
1               5

<210> SEQ ID NO 5
<211> LENGTH: 7
<212> TYPE: PRT
<213> ORGANISM: Artificial Sequence
<220> FEATURE:
<223> OTHER INFORMATION: Novel peptide

<400> SEQUENCE: 5

Lys Tyr Gln Arg Lys Lys Lys
1               5

<210> SEQ ID NO 6
<211> LENGTH: 7
<212> TYPE: PRT
<213> ORGANISM: Artificial Sequence
<220> FEATURE:
<223> OTHER INFORMATION: Novel peptide

<400> SEQUENCE: 6

Lys Tyr Gln Arg Lys Arg Lys
1               5

<210> SEQ ID NO 7
<211> LENGTH: 7
<212> TYPE: PRT
<213> ORGANISM: Artificial Sequence
<220> FEATURE:
<223> OTHER INFORMATION: Novel peptide

<400> SEQUENCE: 7

Lys Tyr Gln Arg Lys Lys Arg
1               5

<210> SEQ ID NO 8
<211> LENGTH: 7
<212> TYPE: PRT
<213> ORGANISM: Artificial Sequence
<220> FEATURE:
<223> OTHER INFORMATION: Novel peptide

<400> SEQUENCE: 8

Lys Tyr Gln Arg Lys Arg Arg
1               5
```

```
<210> SEQ ID NO 9
<211> LENGTH: 7
<212> TYPE: PRT
<213> ORGANISM: Artificial Sequence
<220> FEATURE:
<223> OTHER INFORMATION: Novel peptide

<400> SEQUENCE: 9

Lys Tyr Arg Gln Arg Lys Lys
1               5

<210> SEQ ID NO 10
<211> LENGTH: 7
<212> TYPE: PRT
<213> ORGANISM: Artificial Sequence
<220> FEATURE:
<223> OTHER INFORMATION: Novel peptide

<400> SEQUENCE: 10

Lys Tyr Arg Gln Arg Lys Arg
1               5

<210> SEQ ID NO 11
<211> LENGTH: 7
<212> TYPE: PRT
<213> ORGANISM: Artificial Sequence
<220> FEATURE:
<223> OTHER INFORMATION: Novel peptide

<400> SEQUENCE: 11

Lys Tyr Arg Gln Arg Arg Lys
1               5

<210> SEQ ID NO 12
<211> LENGTH: 7
<212> TYPE: PRT
<213> ORGANISM: Artificial Sequence
<220> FEATURE:
<223> OTHER INFORMATION: Novel peptide

<400> SEQUENCE: 12

Lys Tyr Arg Gln Arg Arg Arg
1               5

<210> SEQ ID NO 13
<211> LENGTH: 7
<212> TYPE: PRT
<213> ORGANISM: Artificial Sequence
<220> FEATURE:
<223> OTHER INFORMATION: Novel peptide

<400> SEQUENCE: 13

Lys Tyr Arg Gln Lys Lys Lys
1               5

<210> SEQ ID NO 14
<211> LENGTH: 7
<212> TYPE: PRT
<213> ORGANISM: Artificial Sequence
<220> FEATURE:
<223> OTHER INFORMATION: Novel peptide

<400> SEQUENCE: 14

Lys Tyr Arg Gln Lys Arg Lys
1               5

<210> SEQ ID NO 15
```

```
<211> LENGTH: 7
<212> TYPE: PRT
<213> ORGANISM: Artificial Sequence
<220> FEATURE:
<223> OTHER INFORMATION: Novel peptide

<400> SEQUENCE: 15

Lys Tyr Arg Gln Lys Lys Arg
1               5

<210> SEQ ID NO 16
<211> LENGTH: 7
<212> TYPE: PRT
<213> ORGANISM: Artificial Sequence
<220> FEATURE:
<223> OTHER INFORMATION: Novel peptide

<400> SEQUENCE: 16

Lys Tyr Arg Gln Lys Arg Arg
1               5

<210> SEQ ID NO 17
<211> LENGTH: 7
<212> TYPE: PRT
<213> ORGANISM: Artificial Sequence
<220> FEATURE:
<223> OTHER INFORMATION: Novel peptide

<400> SEQUENCE: 17

Lys Tyr Lys Gln Arg Lys Lys
1               5

<210> SEQ ID NO 18
<211> LENGTH: 7
<212> TYPE: PRT
<213> ORGANISM: Artificial Sequence
<220> FEATURE:
<223> OTHER INFORMATION: Novel peptide

<400> SEQUENCE: 18

Lys Tyr Lys Gln Arg Lys Arg
1               5

<210> SEQ ID NO 19
<211> LENGTH: 7
<212> TYPE: PRT
<213> ORGANISM: Artificial Sequence
<220> FEATURE:
<223> OTHER INFORMATION: Novel peptide

<400> SEQUENCE: 19

Lys Tyr Lys Gln Arg Arg Lys
1               5

<210> SEQ ID NO 20
<211> LENGTH: 7
<212> TYPE: PRT
<213> ORGANISM: Artificial Sequence
<220> FEATURE:
<223> OTHER INFORMATION: Novel peptide

<400> SEQUENCE: 20

Lys Tyr Lys Gln Arg Arg Arg
1               5

<210> SEQ ID NO 21
<211> LENGTH: 7
```

```
<212> TYPE: PRT
<213> ORGANISM: Artificial Sequence
<220> FEATURE:
<223> OTHER INFORMATION: Novel peptide

<400> SEQUENCE: 21

Lys Tyr Lys Gln Lys Lys Lys
1               5

<210> SEQ ID NO 22
<211> LENGTH: 7
<212> TYPE: PRT
<213> ORGANISM: Artificial Sequence
<220> FEATURE:
<223> OTHER INFORMATION: Novel peptide

<400> SEQUENCE: 22

Lys Tyr Lys Gln Lys Arg Lys
1               5

<210> SEQ ID NO 23
<211> LENGTH: 7
<212> TYPE: PRT
<213> ORGANISM: Artificial Sequence
<220> FEATURE:
<223> OTHER INFORMATION: Novel peptide

<400> SEQUENCE: 23

Lys Tyr Lys Gln Lys Lys Arg
1               5

<210> SEQ ID NO 24
<211> LENGTH: 7
<212> TYPE: PRT
<213> ORGANISM: Artificial Sequence
<220> FEATURE:
<223> OTHER INFORMATION: Novel peptide

<400> SEQUENCE: 24

Lys Tyr Lys Gln Lys Arg Arg
1               5

<210> SEQ ID NO 25
<211> LENGTH: 7
<212> TYPE: PRT
<213> ORGANISM: Artificial Sequence
<220> FEATURE:
<223> OTHER INFORMATION: Novel peptide

<400> SEQUENCE: 25

Lys Tyr Gln Gln Arg Lys Lys
1               5

<210> SEQ ID NO 26
<211> LENGTH: 7
<212> TYPE: PRT
<213> ORGANISM: Artificial Sequence
<220> FEATURE:
<223> OTHER INFORMATION: Novel peptide

<400> SEQUENCE: 26

Lys Tyr Gln Gln Arg Lys Arg
1               5

<210> SEQ ID NO 27
<211> LENGTH: 7
<212> TYPE: PRT
```

```
<213> ORGANISM: Artificial Sequence
<220> FEATURE:
<223> OTHER INFORMATION: Novel peptide

<400> SEQUENCE: 27

Lys Tyr Gln Gln Arg Arg Lys
1               5

<210> SEQ ID NO 28
<211> LENGTH: 7
<212> TYPE: PRT
<213> ORGANISM: Artificial Sequence
<220> FEATURE:
<223> OTHER INFORMATION: Novel peptide

<400> SEQUENCE: 28

Lys Tyr Gln Gln Arg Arg Arg
1               5

<210> SEQ ID NO 29
<211> LENGTH: 7
<212> TYPE: PRT
<213> ORGANISM: Artificial Sequence
<220> FEATURE:
<223> OTHER INFORMATION: Novel peptide

<400> SEQUENCE: 29

Lys Tyr Gln Gln Lys Lys Lys
1               5

<210> SEQ ID NO 30
<211> LENGTH: 7
<212> TYPE: PRT
<213> ORGANISM: Artificial Sequence
<220> FEATURE:
<223> OTHER INFORMATION: Novel peptide

<400> SEQUENCE: 30

Lys Tyr Gln Gln Lys Arg Lys
1               5

<210> SEQ ID NO 31
<211> LENGTH: 7
<212> TYPE: PRT
<213> ORGANISM: Artificial Sequence
<220> FEATURE:
<223> OTHER INFORMATION: Novel peptide

<400> SEQUENCE: 31

Lys Tyr Gln Gln Lys Lys Arg
1               5

<210> SEQ ID NO 32
<211> LENGTH: 7
<212> TYPE: PRT
<213> ORGANISM: Artificial Sequence
<220> FEATURE:
<223> OTHER INFORMATION: Novel peptide

<400> SEQUENCE: 32

Lys Tyr Gln Gln Lys Arg Arg
1               5

<210> SEQ ID NO 33
<211> LENGTH: 7
<212> TYPE: PRT
<213> ORGANISM: Artificial Sequence
```

<220> FEATURE:
<223> OTHER INFORMATION: Novel peptide

<400> SEQUENCE: 33

Lys Tyr Arg Arg Arg Lys Lys
1               5

<210> SEQ ID NO 34
<211> LENGTH: 7
<212> TYPE: PRT
<213> ORGANISM: Artificial Sequence
<220> FEATURE:
<223> OTHER INFORMATION: Novel peptide

<400> SEQUENCE: 34

Lys Tyr Arg Arg Arg Lys Arg
1               5

<210> SEQ ID NO 35
<211> LENGTH: 7
<212> TYPE: PRT
<213> ORGANISM: Artificial Sequence
<220> FEATURE:
<223> OTHER INFORMATION: Novel peptide

<400> SEQUENCE: 35

Lys Tyr Arg Arg Arg Arg Lys
1               5

<210> SEQ ID NO 36
<211> LENGTH: 7
<212> TYPE: PRT
<213> ORGANISM: Artificial Sequence
<220> FEATURE:
<223> OTHER INFORMATION: Novel peptide

<400> SEQUENCE: 36

Lys Tyr Arg Arg Arg Arg Arg
1               5

<210> SEQ ID NO 37
<211> LENGTH: 7
<212> TYPE: PRT
<213> ORGANISM: Artificial Sequence
<220> FEATURE:
<223> OTHER INFORMATION: Novel peptide

<400> SEQUENCE: 37

Lys Tyr Arg Arg Lys Lys Lys
1               5

<210> SEQ ID NO 38
<211> LENGTH: 7
<212> TYPE: PRT
<213> ORGANISM: Artificial Sequence
<220> FEATURE:
<223> OTHER INFORMATION: Novel peptide

<400> SEQUENCE: 38

Lys Tyr Arg Arg Lys Arg Lys
1               5

<210> SEQ ID NO 39
<211> LENGTH: 7
<212> TYPE: PRT
<213> ORGANISM: Artificial Sequence
<220> FEATURE:

<223> OTHER INFORMATION: Novel peptide

<400> SEQUENCE: 39

Lys Tyr Arg Arg Lys Lys Arg
1               5

<210> SEQ ID NO 40
<211> LENGTH: 7
<212> TYPE: PRT
<213> ORGANISM: Artificial Sequence
<220> FEATURE:
<223> OTHER INFORMATION: Novel peptide

<400> SEQUENCE: 40

Lys Tyr Arg Arg Lys Arg Arg
1               5

<210> SEQ ID NO 41
<211> LENGTH: 7
<212> TYPE: PRT
<213> ORGANISM: Artificial Sequence
<220> FEATURE:
<223> OTHER INFORMATION: Novel peptide

<400> SEQUENCE: 41

Lys Tyr Lys Arg Arg Lys Lys
1               5

<210> SEQ ID NO 42
<211> LENGTH: 7
<212> TYPE: PRT
<213> ORGANISM: Artificial Sequence
<220> FEATURE:
<223> OTHER INFORMATION: Novel peptide

<400> SEQUENCE: 42

Lys Tyr Lys Arg Arg Lys Arg
1               5

<210> SEQ ID NO 43
<211> LENGTH: 7
<212> TYPE: PRT
<213> ORGANISM: Artificial Sequence
<220> FEATURE:
<223> OTHER INFORMATION: Novel peptide

<400> SEQUENCE: 43

Lys Tyr Lys Arg Arg Arg Lys
1               5

<210> SEQ ID NO 44
<211> LENGTH: 7
<212> TYPE: PRT
<213> ORGANISM: Artificial Sequence
<220> FEATURE:
<223> OTHER INFORMATION: Novel peptide

<400> SEQUENCE: 44

Lys Tyr Lys Arg Arg Arg Arg
1               5

<210> SEQ ID NO 45
<211> LENGTH: 7
<212> TYPE: PRT
<213> ORGANISM: Artificial Sequence
<220> FEATURE:
<223> OTHER INFORMATION: Novel peptide

<400> SEQUENCE: 45

Lys Tyr Lys Arg Lys Lys Lys
1               5

<210> SEQ ID NO 46
<211> LENGTH: 7
<212> TYPE: PRT
<213> ORGANISM: Artificial Sequence
<220> FEATURE:
<223> OTHER INFORMATION: Novel peptide

<400> SEQUENCE: 46

Lys Tyr Lys Arg Lys Arg Lys
1               5

<210> SEQ ID NO 47
<211> LENGTH: 7
<212> TYPE: PRT
<213> ORGANISM: Artificial Sequence
<220> FEATURE:
<223> OTHER INFORMATION: Novel peptide

<400> SEQUENCE: 47

Lys Tyr Lys Arg Lys Lys Arg
1               5

<210> SEQ ID NO 48
<211> LENGTH: 7
<212> TYPE: PRT
<213> ORGANISM: Artificial Sequence
<220> FEATURE:
<223> OTHER INFORMATION: Novel peptide

<400> SEQUENCE: 48

Lys Tyr Lys Arg Lys Arg Arg
1               5

<210> SEQ ID NO 49
<211> LENGTH: 7
<212> TYPE: PRT
<213> ORGANISM: Artificial Sequence
<220> FEATURE:
<223> OTHER INFORMATION: Novel peptide

<400> SEQUENCE: 49

Lys Tyr Gln Lys Arg Lys Lys
1               5

<210> SEQ ID NO 50
<211> LENGTH: 7
<212> TYPE: PRT
<213> ORGANISM: Artificial Sequence
<220> FEATURE:
<223> OTHER INFORMATION: Novel peptide

<400> SEQUENCE: 50

Lys Tyr Gln Lys Arg Lys Arg
1               5

<210> SEQ ID NO 51
<211> LENGTH: 7
<212> TYPE: PRT
<213> ORGANISM: Artificial Sequence
<220> FEATURE:
<223> OTHER INFORMATION: Novel peptide

```
<400> SEQUENCE: 51

Lys Tyr Gln Lys Arg Arg Lys
1               5

<210> SEQ ID NO 52
<211> LENGTH: 7
<212> TYPE: PRT
<213> ORGANISM: Artificial Sequence
<220> FEATURE:
<223> OTHER INFORMATION: Novel peptide

<400> SEQUENCE: 52

Lys Tyr Gln Lys Arg Arg Arg
1               5

<210> SEQ ID NO 53
<211> LENGTH: 7
<212> TYPE: PRT
<213> ORGANISM: Artificial Sequence
<220> FEATURE:
<223> OTHER INFORMATION: Novel peptide

<400> SEQUENCE: 53

Lys Tyr Gln Lys Lys Lys Lys
1               5

<210> SEQ ID NO 54
<211> LENGTH: 7
<212> TYPE: PRT
<213> ORGANISM: Artificial Sequence
<220> FEATURE:
<223> OTHER INFORMATION: Novel peptide

<400> SEQUENCE: 54

Lys Tyr Gln Lys Lys Arg Lys
1               5

<210> SEQ ID NO 55
<211> LENGTH: 7
<212> TYPE: PRT
<213> ORGANISM: Artificial Sequence
<220> FEATURE:
<223> OTHER INFORMATION: Novel peptide

<400> SEQUENCE: 55

Lys Tyr Gln Lys Lys Lys Arg
1               5

<210> SEQ ID NO 56
<211> LENGTH: 7
<212> TYPE: PRT
<213> ORGANISM: Artificial Sequence
<220> FEATURE:
<223> OTHER INFORMATION: Novel peptide

<400> SEQUENCE: 56

Lys Tyr Gln Lys Lys Arg Arg
1               5

<210> SEQ ID NO 57
<211> LENGTH: 7
<212> TYPE: PRT
<213> ORGANISM: Artificial Sequence
<220> FEATURE:
<223> OTHER INFORMATION: Novel peptide

<400> SEQUENCE: 57
```

Lys Tyr Asn Lys Arg Lys Lys
1               5

<210> SEQ ID NO 58
<211> LENGTH: 7
<212> TYPE: PRT
<213> ORGANISM: Artificial Sequence
<220> FEATURE:
<223> OTHER INFORMATION: Novel peptide

<400> SEQUENCE: 58

Lys Tyr Asn Lys Arg Lys Arg
1               5

<210> SEQ ID NO 59
<211> LENGTH: 7
<212> TYPE: PRT
<213> ORGANISM: Artificial Sequence
<220> FEATURE:
<223> OTHER INFORMATION: Novel peptide

<400> SEQUENCE: 59

Lys Tyr Asn Lys Arg Arg Lys
1               5

<210> SEQ ID NO 60
<211> LENGTH: 7
<212> TYPE: PRT
<213> ORGANISM: Artificial Sequence
<220> FEATURE:
<223> OTHER INFORMATION: Novel peptide

<400> SEQUENCE: 60

Lys Tyr Asn Lys Arg Arg Arg
1               5

<210> SEQ ID NO 61
<211> LENGTH: 7
<212> TYPE: PRT
<213> ORGANISM: Artificial Sequence
<220> FEATURE:
<223> OTHER INFORMATION: Novel peptide

<400> SEQUENCE: 61

Lys Tyr Asn Lys Lys Lys Lys
1               5

<210> SEQ ID NO 62
<211> LENGTH: 7
<212> TYPE: PRT
<213> ORGANISM: Artificial Sequence
<220> FEATURE:
<223> OTHER INFORMATION: Novel peptide

<400> SEQUENCE: 62

Lys Tyr Asn Lys Lys Arg Lys
1               5

<210> SEQ ID NO 63
<211> LENGTH: 7
<212> TYPE: PRT
<213> ORGANISM: Artificial Sequence
<220> FEATURE:
<223> OTHER INFORMATION: Novel peptide

<400> SEQUENCE: 63

```
Lys Tyr Asn Lys Lys Lys Arg
1               5

<210> SEQ ID NO 64
<211> LENGTH: 7
<212> TYPE: PRT
<213> ORGANISM: Artificial Sequence
<220> FEATURE:
<223> OTHER INFORMATION: Novel peptide

<400> SEQUENCE: 64

Lys Tyr Asn Lys Lys Arg Arg
1               5

<210> SEQ ID NO 65
<211> LENGTH: 7
<212> TYPE: PRT
<213> ORGANISM: Artificial Sequence
<220> FEATURE:
<223> OTHER INFORMATION: Novel peptide

<400> SEQUENCE: 65

Lys Tyr Asn Arg Arg Lys Lys
1               5

<210> SEQ ID NO 66
<211> LENGTH: 7
<212> TYPE: PRT
<213> ORGANISM: Artificial Sequence
<220> FEATURE:
<223> OTHER INFORMATION: Novel peptide

<400> SEQUENCE: 66

Lys Tyr Asn Arg Arg Lys Arg
1               5

<210> SEQ ID NO 67
<211> LENGTH: 7
<212> TYPE: PRT
<213> ORGANISM: Artificial Sequence
<220> FEATURE:
<223> OTHER INFORMATION: Novel peptide

<400> SEQUENCE: 67

Lys Tyr Asn Arg Arg Arg Lys
1               5

<210> SEQ ID NO 68
<211> LENGTH: 7
<212> TYPE: PRT
<213> ORGANISM: Artificial Sequence
<220> FEATURE:
<223> OTHER INFORMATION: Novel peptide

<400> SEQUENCE: 68

Lys Tyr Asn Arg Arg Arg Arg
1               5

<210> SEQ ID NO 69
<211> LENGTH: 7
<212> TYPE: PRT
<213> ORGANISM: Artificial Sequence
<220> FEATURE:
<223> OTHER INFORMATION: Novel peptide

<400> SEQUENCE: 69

Lys Tyr Asn Arg Lys Lys Lys
```

```
1               5

<210> SEQ ID NO 70
<211> LENGTH: 7
<212> TYPE: PRT
<213> ORGANISM: Artificial Sequence
<220> FEATURE:
<223> OTHER INFORMATION: Novel peptide

<400> SEQUENCE: 70

Lys Tyr Asn Arg Lys Arg Lys
1               5

<210> SEQ ID NO 71
<211> LENGTH: 7
<212> TYPE: PRT
<213> ORGANISM: Artificial Sequence
<220> FEATURE:
<223> OTHER INFORMATION: Novel peptide

<400> SEQUENCE: 71

Lys Tyr Asn Arg Lys Lys Arg
1               5

<210> SEQ ID NO 72
<211> LENGTH: 7
<212> TYPE: PRT
<213> ORGANISM: Artificial Sequence
<220> FEATURE:
<223> OTHER INFORMATION: Novel peptide

<400> SEQUENCE: 72

Lys Tyr Asn Arg Lys Arg Arg
1               5

<210> SEQ ID NO 73
<211> LENGTH: 7
<212> TYPE: PRT
<213> ORGANISM: Artificial Sequence
<220> FEATURE:
<223> OTHER INFORMATION: Novel peptide

<400> SEQUENCE: 73

Lys Tyr Arg Asn Arg Lys Lys
1               5

<210> SEQ ID NO 74
<211> LENGTH: 7
<212> TYPE: PRT
<213> ORGANISM: Artificial Sequence
<220> FEATURE:
<223> OTHER INFORMATION: Novel peptide

<400> SEQUENCE: 74

Lys Tyr Arg Asn Arg Lys Arg
1               5

<210> SEQ ID NO 75
<211> LENGTH: 7
<212> TYPE: PRT
<213> ORGANISM: Artificial Sequence
<220> FEATURE:
<223> OTHER INFORMATION: Novel peptide

<400> SEQUENCE: 75

Lys Tyr Arg Asn Arg Arg Lys
1               5
```

```
<210> SEQ ID NO 76
<211> LENGTH: 7
<212> TYPE: PRT
<213> ORGANISM: Artificial Sequence
<220> FEATURE:
<223> OTHER INFORMATION: Novel peptide

<400> SEQUENCE: 76

Lys Tyr Arg Asn Arg Arg Arg
1               5

<210> SEQ ID NO 77
<211> LENGTH: 7
<212> TYPE: PRT
<213> ORGANISM: Artificial Sequence
<220> FEATURE:
<223> OTHER INFORMATION: Novel peptide

<400> SEQUENCE: 77

Lys Tyr Arg Asn Lys Lys Lys
1               5

<210> SEQ ID NO 78
<211> LENGTH: 7
<212> TYPE: PRT
<213> ORGANISM: Artificial Sequence
<220> FEATURE:
<223> OTHER INFORMATION: Novel peptide

<400> SEQUENCE: 78

Lys Tyr Arg Asn Lys Arg Lys
1               5

<210> SEQ ID NO 79
<211> LENGTH: 7
<212> TYPE: PRT
<213> ORGANISM: Artificial Sequence
<220> FEATURE:
<223> OTHER INFORMATION: Novel peptide

<400> SEQUENCE: 79

Lys Tyr Arg Asn Lys Lys Arg
1               5

<210> SEQ ID NO 80
<211> LENGTH: 7
<212> TYPE: PRT
<213> ORGANISM: Artificial Sequence
<220> FEATURE:
<223> OTHER INFORMATION: Novel peptide

<400> SEQUENCE: 80

Lys Tyr Arg Asn Lys Arg Arg
1               5

<210> SEQ ID NO 81
<211> LENGTH: 7
<212> TYPE: PRT
<213> ORGANISM: Artificial Sequence
<220> FEATURE:
<223> OTHER INFORMATION: Novel peptide

<400> SEQUENCE: 81

Lys Tyr Lys Asn Arg Lys Lys
1               5
```

```
<210> SEQ ID NO 82
<211> LENGTH: 7
<212> TYPE: PRT
<213> ORGANISM: Artificial Sequence
<220> FEATURE:
<223> OTHER INFORMATION: Novel peptide

<400> SEQUENCE: 82

Lys Tyr Lys Asn Arg Lys Arg
1               5

<210> SEQ ID NO 83
<211> LENGTH: 7
<212> TYPE: PRT
<213> ORGANISM: Artificial Sequence
<220> FEATURE:
<223> OTHER INFORMATION: Novel peptide

<400> SEQUENCE: 83

Lys Tyr Lys Asn Arg Arg Lys
1               5

<210> SEQ ID NO 84
<211> LENGTH: 7
<212> TYPE: PRT
<213> ORGANISM: Artificial Sequence
<220> FEATURE:
<223> OTHER INFORMATION: Novel peptide

<400> SEQUENCE: 84

Lys Tyr Lys Asn Arg Arg Arg
1               5

<210> SEQ ID NO 85
<211> LENGTH: 7
<212> TYPE: PRT
<213> ORGANISM: Artificial Sequence
<220> FEATURE:
<223> OTHER INFORMATION: Novel peptide

<400> SEQUENCE: 85

Lys Tyr Lys Asn Lys Lys Lys
1               5

<210> SEQ ID NO 86
<211> LENGTH: 7
<212> TYPE: PRT
<213> ORGANISM: Artificial Sequence
<220> FEATURE:
<223> OTHER INFORMATION: Novel peptide

<400> SEQUENCE: 86

Lys Tyr Lys Asn Lys Arg Lys
1               5

<210> SEQ ID NO 87
<211> LENGTH: 7
<212> TYPE: PRT
<213> ORGANISM: Artificial Sequence
<220> FEATURE:
<223> OTHER INFORMATION: Novel peptide

<400> SEQUENCE: 87

Lys Tyr Lys Asn Lys Lys Arg
1               5
```

```
<210> SEQ ID NO 88
<211> LENGTH: 7
<212> TYPE: PRT
<213> ORGANISM: Artificial Sequence
<220> FEATURE:
<223> OTHER INFORMATION: Novel peptide

<400> SEQUENCE: 88

Lys Tyr Lys Asn Lys Arg Arg
1               5

<210> SEQ ID NO 89
<211> LENGTH: 7
<212> TYPE: PRT
<213> ORGANISM: Artificial Sequence
<220> FEATURE:
<223> OTHER INFORMATION: Novel peptide

<400> SEQUENCE: 89

Lys Tyr Gln Asn Arg Lys Lys
1               5

<210> SEQ ID NO 90
<211> LENGTH: 7
<212> TYPE: PRT
<213> ORGANISM: Artificial Sequence
<220> FEATURE:
<223> OTHER INFORMATION: Novel peptide

<400> SEQUENCE: 90

Lys Tyr Gln Asn Arg Lys Arg
1               5

<210> SEQ ID NO 91
<211> LENGTH: 7
<212> TYPE: PRT
<213> ORGANISM: Artificial Sequence
<220> FEATURE:
<223> OTHER INFORMATION: Novel peptide

<400> SEQUENCE: 91

Lys Tyr Gln Asn Arg Arg Lys
1               5

<210> SEQ ID NO 92
<211> LENGTH: 7
<212> TYPE: PRT
<213> ORGANISM: Artificial Sequence
<220> FEATURE:
<223> OTHER INFORMATION: Novel peptide

<400> SEQUENCE: 92

Lys Tyr Gln Asn Arg Arg Arg
1               5

<210> SEQ ID NO 93
<211> LENGTH: 7
<212> TYPE: PRT
<213> ORGANISM: Artificial Sequence
<220> FEATURE:
<223> OTHER INFORMATION: Novel peptide

<400> SEQUENCE: 93

Lys Tyr Gln Asn Lys Lys Lys
1               5

<210> SEQ ID NO 94
```

```
<211> LENGTH: 7
<212> TYPE: PRT
<213> ORGANISM: Artificial Sequence
<220> FEATURE:
<223> OTHER INFORMATION: Novel peptide

<400> SEQUENCE: 94

Lys Tyr Gln Asn Lys Arg Lys
1               5

<210> SEQ ID NO 95
<211> LENGTH: 7
<212> TYPE: PRT
<213> ORGANISM: Artificial Sequence
<220> FEATURE:
<223> OTHER INFORMATION: Novel peptide

<400> SEQUENCE: 95

Lys Tyr Gln Asn Lys Lys Arg
1               5

<210> SEQ ID NO 96
<211> LENGTH: 7
<212> TYPE: PRT
<213> ORGANISM: Artificial Sequence
<220> FEATURE:
<223> OTHER INFORMATION: Novel peptide

<400> SEQUENCE: 96

Lys Tyr Gln Asn Lys Arg Arg
1               5

<210> SEQ ID NO 97
<211> LENGTH: 7
<212> TYPE: PRT
<213> ORGANISM: Artificial Sequence
<220> FEATURE:
<223> OTHER INFORMATION: Novel peptide

<400> SEQUENCE: 97

Lys Tyr Asn Gln Arg Lys Lys
1               5

<210> SEQ ID NO 98
<211> LENGTH: 7
<212> TYPE: PRT
<213> ORGANISM: Artificial Sequence
<220> FEATURE:
<223> OTHER INFORMATION: Novel peptide

<400> SEQUENCE: 98

Lys Tyr Asn Gln Arg Lys Arg
1               5

<210> SEQ ID NO 99
<211> LENGTH: 7
<212> TYPE: PRT
<213> ORGANISM: Artificial Sequence
<220> FEATURE:
<223> OTHER INFORMATION: Novel peptide

<400> SEQUENCE: 99

Lys Tyr Asn Gln Arg Arg Lys
1               5

<210> SEQ ID NO 100
<211> LENGTH: 7
```

```
<212> TYPE: PRT
<213> ORGANISM: Artificial Sequence
<220> FEATURE:
<223> OTHER INFORMATION: Novel peptide

<400> SEQUENCE: 100

Lys Tyr Asn Gln Arg Arg Arg
1               5

<210> SEQ ID NO 101
<211> LENGTH: 7
<212> TYPE: PRT
<213> ORGANISM: Artificial Sequence
<220> FEATURE:
<223> OTHER INFORMATION: Novel peptide

<400> SEQUENCE: 101

Lys Tyr Asn Gln Lys Lys Lys
1               5

<210> SEQ ID NO 102
<211> LENGTH: 7
<212> TYPE: PRT
<213> ORGANISM: Artificial Sequence
<220> FEATURE:
<223> OTHER INFORMATION: Novel peptide

<400> SEQUENCE: 102

Lys Tyr Asn Gln Lys Arg Lys
1               5

<210> SEQ ID NO 103
<211> LENGTH: 7
<212> TYPE: PRT
<213> ORGANISM: Artificial Sequence
<220> FEATURE:
<223> OTHER INFORMATION: Novel peptide

<400> SEQUENCE: 103

Lys Tyr Asn Gln Lys Lys Arg
1               5

<210> SEQ ID NO 104
<211> LENGTH: 7
<212> TYPE: PRT
<213> ORGANISM: Artificial Sequence
<220> FEATURE:
<223> OTHER INFORMATION: Novel peptide

<400> SEQUENCE: 104

Lys Tyr Asn Gln Lys Arg Arg
1               5

<210> SEQ ID NO 105
<211> LENGTH: 7
<212> TYPE: PRT
<213> ORGANISM: Artificial Sequence
<220> FEATURE:
<223> OTHER INFORMATION: Novel peptide

<400> SEQUENCE: 105

Lys Tyr Asn Asn Arg Lys Lys
1               5

<210> SEQ ID NO 106
<211> LENGTH: 7
<212> TYPE: PRT
```

```
<213> ORGANISM: Artificial Sequence
<220> FEATURE:
<223> OTHER INFORMATION: Novel peptide

<400> SEQUENCE: 106

Lys Tyr Asn Asn Arg Lys Arg
1               5

<210> SEQ ID NO 107
<211> LENGTH: 7
<212> TYPE: PRT
<213> ORGANISM: Artificial Sequence
<220> FEATURE:
<223> OTHER INFORMATION: Novel peptide

<400> SEQUENCE: 107

Lys Tyr Asn Asn Arg Arg Lys
1               5

<210> SEQ ID NO 108
<211> LENGTH: 7
<212> TYPE: PRT
<213> ORGANISM: Artificial Sequence
<220> FEATURE:
<223> OTHER INFORMATION: Novel peptide

<400> SEQUENCE: 108

Lys Tyr Asn Asn Arg Arg Arg
1               5

<210> SEQ ID NO 109
<211> LENGTH: 7
<212> TYPE: PRT
<213> ORGANISM: Artificial Sequence
<220> FEATURE:
<223> OTHER INFORMATION: Novel peptide

<400> SEQUENCE: 109

Lys Tyr Asn Asn Lys Lys Lys
1               5

<210> SEQ ID NO 110
<211> LENGTH: 7
<212> TYPE: PRT
<213> ORGANISM: Artificial Sequence
<220> FEATURE:
<223> OTHER INFORMATION: Novel peptide

<400> SEQUENCE: 110

Lys Tyr Asn Asn Lys Arg Lys
1               5

<210> SEQ ID NO 111
<211> LENGTH: 7
<212> TYPE: PRT
<213> ORGANISM: Artificial Sequence
<220> FEATURE:
<223> OTHER INFORMATION: Novel peptide

<400> SEQUENCE: 111

Lys Tyr Asn Asn Lys Lys Arg
1               5

<210> SEQ ID NO 112
<211> LENGTH: 7
<212> TYPE: PRT
<213> ORGANISM: Artificial Sequence
```

```
<220> FEATURE:
<223> OTHER INFORMATION: Novel peptide

<400> SEQUENCE: 112

Lys Tyr Asn Asn Lys Arg Arg
1               5

<210> SEQ ID NO 113
<211> LENGTH: 7
<212> TYPE: PRT
<213> ORGANISM: Artificial Sequence
<220> FEATURE:
<223> OTHER INFORMATION: Novel peptide

<400> SEQUENCE: 113

Lys Tyr Arg Lys Arg Lys Lys
1               5

<210> SEQ ID NO 114
<211> LENGTH: 7
<212> TYPE: PRT
<213> ORGANISM: Artificial Sequence
<220> FEATURE:
<223> OTHER INFORMATION: Novel peptide

<400> SEQUENCE: 114

Lys Tyr Arg Lys Arg Lys Arg
1               5

<210> SEQ ID NO 115
<211> LENGTH: 7
<212> TYPE: PRT
<213> ORGANISM: Artificial Sequence
<220> FEATURE:
<223> OTHER INFORMATION: Novel peptide

<400> SEQUENCE: 115

Lys Tyr Arg Lys Arg Arg Lys
1               5

<210> SEQ ID NO 116
<211> LENGTH: 7
<212> TYPE: PRT
<213> ORGANISM: Artificial Sequence
<220> FEATURE:
<223> OTHER INFORMATION: Novel peptide

<400> SEQUENCE: 116

Lys Tyr Arg Lys Arg Arg Arg
1               5

<210> SEQ ID NO 117
<211> LENGTH: 7
<212> TYPE: PRT
<213> ORGANISM: Artificial Sequence
<220> FEATURE:
<223> OTHER INFORMATION: Novel peptide

<400> SEQUENCE: 117

Lys Tyr Arg Lys Lys Lys Lys
1               5

<210> SEQ ID NO 118
<211> LENGTH: 7
<212> TYPE: PRT
<213> ORGANISM: Artificial Sequence
<220> FEATURE:
```

```
<223> OTHER INFORMATION: Novel peptide

<400> SEQUENCE: 118

Lys Tyr Arg Lys Lys Arg Lys
1               5

<210> SEQ ID NO 119
<211> LENGTH: 7
<212> TYPE: PRT
<213> ORGANISM: Artificial Sequence
<220> FEATURE:
<223> OTHER INFORMATION: Novel peptide

<400> SEQUENCE: 119

Lys Tyr Arg Asn Lys Lys Arg
1               5

<210> SEQ ID NO 120
<211> LENGTH: 7
<212> TYPE: PRT
<213> ORGANISM: Artificial Sequence
<220> FEATURE:
<223> OTHER INFORMATION: Novel peptide

<400> SEQUENCE: 120

Lys Tyr Arg Asn Lys Arg Arg
1               5

<210> SEQ ID NO 121
<211> LENGTH: 7
<212> TYPE: PRT
<213> ORGANISM: Artificial Sequence
<220> FEATURE:
<223> OTHER INFORMATION: Novel peptide

<400> SEQUENCE: 121

Lys Tyr Lys Lys Arg Lys Lys
1               5

<210> SEQ ID NO 122
<211> LENGTH: 7
<212> TYPE: PRT
<213> ORGANISM: Artificial Sequence
<220> FEATURE:
<223> OTHER INFORMATION: Novel peptide

<400> SEQUENCE: 122

Lys Tyr Lys Lys Arg Lys Arg
1               5

<210> SEQ ID NO 123
<211> LENGTH: 7
<212> TYPE: PRT
<213> ORGANISM: Artificial Sequence
<220> FEATURE:
<223> OTHER INFORMATION: Novel peptide

<400> SEQUENCE: 123

Lys Tyr Lys Lys Arg Arg Lys
1               5

<210> SEQ ID NO 124
<211> LENGTH: 7
<212> TYPE: PRT
<213> ORGANISM: Artificial Sequence
<220> FEATURE:
<223> OTHER INFORMATION: Novel peptide
```

<400> SEQUENCE: 124

Lys Tyr Lys Lys Arg Arg Arg
1               5

<210> SEQ ID NO 125
<211> LENGTH: 7
<212> TYPE: PRT
<213> ORGANISM: Artificial Sequence
<220> FEATURE:
<223> OTHER INFORMATION: Novel peptide

<400> SEQUENCE: 125

Lys Tyr Lys Lys Lys Lys Lys
1               5

<210> SEQ ID NO 126
<211> LENGTH: 7
<212> TYPE: PRT
<213> ORGANISM: Artificial Sequence
<220> FEATURE:
<223> OTHER INFORMATION: Novel peptide

<400> SEQUENCE: 126

Lys Tyr Lys Lys Lys Arg Lys
1               5

<210> SEQ ID NO 127
<211> LENGTH: 7
<212> TYPE: PRT
<213> ORGANISM: Artificial Sequence
<220> FEATURE:
<223> OTHER INFORMATION: Novel peptide

<400> SEQUENCE: 127

Lys Tyr Lys Lys Lys Lys Arg
1               5

<210> SEQ ID NO 128
<211> LENGTH: 7
<212> TYPE: PRT
<213> ORGANISM: Artificial Sequence
<220> FEATURE:
<223> OTHER INFORMATION: Novel peptide

<400> SEQUENCE: 128

Lys Tyr Lys Lys Lys Arg Arg
1               5

<210> SEQ ID NO 129
<211> LENGTH: 23
<212> TYPE: DNA
<213> ORGANISM: Artificial Sequence
<220> FEATURE:
<223> OTHER INFORMATION: Primer

<400> SEQUENCE: 129
caaccataga gaaagcaaac gcg                                           23

<210> SEQ ID NO 130
<211> LENGTH: 22
<212> TYPE: DNA
<213> ORGANISM: Artificial Sequence
<220> FEATURE:
<223> OTHER INFORMATION: Primer

<400> SEQUENCE: 130

-continued tttctgttgc cactgctggg ac                                          22

<210> SEQ ID NO 131
<211> LENGTH: 22
<212> TYPE: DNA
<213> ORGANISM: Artificial Sequence
<220> FEATURE:
<223> OTHER INFORMATION: Primer

<400> SEQUENCE: 131
agccctgacc actccagttt ag                                          22

<210> SEQ ID NO 132
<211> LENGTH: 24
<212> TYPE: DNA
<213> ORGANISM: Artificial Sequence
<220> FEATURE:
<223> OTHER INFORMATION: Primer

<400> SEQUENCE: 132
ccctctatgg ctgtttcttt ctct                                        24

<210> SEQ ID NO 133
<211> LENGTH: 21
<212> TYPE: DNA
<213> ORGANISM: Artificial Sequence
<220> FEATURE:
<223> OTHER INFORMATION: Primer

<400> SEQUENCE: 133
gaatggcctg tgctttctca a                                           21

<210> SEQ ID NO 134
<211> LENGTH: 21
<212> TYPE: DNA
<213> ORGANISM: Artificial Sequence
<220> FEATURE:
<223> OTHER INFORMATION: Primer

<400> SEQUENCE: 134
tcggatgagt cactactgcc c                                           21

<210> SEQ ID NO 135
<211> LENGTH: 18
<212> TYPE: DNA
<213> ORGANISM: Artificial Sequence
<220> FEATURE:
<223> OTHER INFORMATION: Primer

<400> SEQUENCE: 135
ccatggagaa ggctgggg                                               18

<210> SEQ ID NO 136
<211> LENGTH: 20
<212> TYPE: DNA
<213> ORGANISM: Artificial Sequence
<220> FEATURE:
<223> OTHER INFORMATION: Primer

<400> SEQUENCE: 136
caaagttctc atggatgacc                                             20